US010415029B2

(12) United States Patent
Dambacher et al.

(10) Patent No.: US 10,415,029 B2
(45) Date of Patent: Sep. 17, 2019

(54) ALLELE-SPECIFIC CAPTURE OF NUCLEIC ACIDS

(71) Applicant: Omniome, Inc., San Diego, CA (US)

(72) Inventors: Corey M. Dambacher, La Jolla, CA (US); Eugene Tu, San Diego, CA (US)

(73) Assignee: OMNIOME, INC., San Diego, CA (US)

( * ) Notice: Subject to any disclaimer, the term of this patent is extended or adjusted under 35 U.S.C. 154(b) by 261 days.

(21) Appl. No.: 15/701,358

(22) Filed: Sep. 11, 2017

(65) Prior Publication Data
US 2018/0208922 A1    Jul. 26, 2018

Related U.S. Application Data

(60) Provisional application No. 62/448,730, filed on Jan. 20, 2017.

(51) Int. Cl.
| C12P 19/34 | (2006.01) |
| C12N 15/10 | (2006.01) |
| C12Q 1/686 | (2018.01) |
| C12Q 1/6869 | (2018.01) |

(52) U.S. Cl.
CPC ..... C12N 15/1006 (2013.01); C12N 15/1024 (2013.01); C12Q 1/686 (2013.01); C12Q 1/6869 (2013.01)

(58) Field of Classification Search
CPC ............ C12Q 1/6869; C12Q 2521/101; C12Q 2535/125; C12Q 2521/543; C12Q 2527/125; C12Q 2563/137; C12Q 2563/149; C12Q 1/686; C12N 15/1006; C12N 15/1024; C12N 9/1252
See application file for complete search history.

(56) References Cited

U.S. PATENT DOCUMENTS

| 5,679,524 A | 10/1997 | Nikiforov et al. |
| 6,004,744 A | 12/1999 | Goelet et al. |
| 6,013,431 A | 1/2000 | Soderlund et al. |
| 6,150,095 A | 11/2000 | Southern et al. |
| 6,153,379 A | 11/2000 | Caskey et al. |
| 6,280,954 B1 | 8/2001 | Ulfendahl et al. |
| 6,355,431 B1 | 3/2002 | Chee et al. |
| 6,537,748 B1 | 3/2003 | Goelet et al. |
| 6,908,736 B1 | 6/2005 | Densham |
| 7,008,766 B1 | 3/2006 | Densham et al. |
| 7,264,934 B2 | 9/2007 | Fuller et al. |
| 7,476,503 B2 | 1/2009 | Turner et al. |
| 7,604,963 B2 | 10/2009 | Densham et al. |
| 7,888,073 B2 | 2/2011 | Densham et al. |
| 8,133,672 B2 | 3/2012 | Bjornson et al. |
| 8,399,196 B2 | 3/2013 | Hoser et al. |
| 8,632,975 B2 | 1/2014 | Vander Horn et al. |
| 8,652,781 B2 | 2/2014 | Korlach et al. |
| 9,045,796 B2 | 6/2015 | Gunderson et al. |
| 9,279,155 B2 | 3/2016 | Bjornson et al. |
| 9,353,412 B2 | 5/2016 | Pantoja et al. |
| 9,279,154 B2 | 6/2016 | Previte et al. |
| 9,556,480 B2 | 1/2017 | Turner et al. |
| 9,695,471 B2 | 7/2017 | Beechem et al. |
| 9,719,073 B2 | 8/2017 | Emig et al. |
| 9,932,631 B1 | 4/2018 | Dambacher et al. |
| 10,113,197 B2 | 10/2018 | Sun et al. |
| 2006/0051807 A1 | 3/2006 | Fuller |
| 2010/0330570 A1* | 12/2010 | Vander Horn ....... C12Q 1/6827 435/6.11 |
| 2016/0032379 A1 | 2/2016 | Gloeckner et al. |
| 2017/0022553 A1 | 1/2017 | Vijayan et al. |

FOREIGN PATENT DOCUMENTS

WO    2010141390    12/2010

OTHER PUBLICATIONS

Chen et al., "The History and Advances of Reversible Terminators Used in New Generations of Sequencing Technology", Genomics Proteomics Bioinformatics, 11(1), Feb. 1, 2013, pp. 34-40.
Roettger et al., "Mismatched and Matched dNTP Incorporation by DNA Polymerase β Proceed via Analogues Kinetic Pathways", Biochemistry, 47, Sep. 16, 2008, pp. 9718-9727.
Tsai et al., "Site-specific labeling of T7 DNA polymerase with a conformationally sensitive flurophore and its use in detecting single-nucleotide polymorphisms", Analytical Biochemistry, vol. 384, No. 1, Academic Press Inc., New York, Jan. 1, 2009, pp. 136-144.
Fuller et al., "The challenges of sequencing by synthesis", Nature Biotechnology, vol. 27, No. 11, Nov. 2009, pp. 1013-1023.
PCT/US2017/051023 , "International Search Report and Written Opinion", dated Nov. 29, 2017, 14 pages.
Previte et al., "DNA sequencing using polymerase substrate-binding kinetics", Nature Communications, Nature Publishing Group, United Kingdom, vol. 6, Jan. 23, 2015, 12 pages.
Datta, "Salt Dependence of DNA binding by Thermus aquaticus and Escherichia coli DNA Polymerases", Journal of Biological Chemistry, vol. 278, Issue of Feb. 21, 2003, 5694-5701.
Deredge et al., "The Glutamate Effect on DNA Binding by Pol I DNA Polymerases: Osmotic Stress and the Effective Reversal of Salt Linkage," J. Mol. Biol., 2010, vol. 401, pp. 223-238.

(Continued)

Primary Examiner — Cynthia B Wilder
(74) Attorney, Agent, or Firm — Kilpatrick Townsend & Stockton LLP

(57) ABSTRACT

A method for separating a target allele from a mixture of nucleic acids by (a) providing a mixture of nucleic acids in fluidic contact with a stabilized ternary complex that is attached to a solid support, wherein the stabilized ternary complex includes a polymerase, primed nucleic acid template, and next correct nucleotide, wherein the template has a target allele, wherein the next correct nucleotide is a cognate nucleotide for the target allele, and wherein the stabilized ternary complex is attached to the solid support via a linkage between the polymerase and the solid support or via a linkage between the next correct nucleotide and the solid support; and (b) separating the solid support from the mixture of nucleic acids, thereby separating the target allele from the mixture of nucleic acids.

20 Claims, 5 Drawing Sheets

(56) References Cited

OTHER PUBLICATIONS

Klenow et al., "Effect of Monovalent Cations on the Activity of the DNA Polymerase of *Escherichia coli* B", European J. Biochem., 1696, 133-141.

Nikiforov et al., "Genetic Bit Analysis: a solid phase method for typing single nucleotide polymorphisms", Nucl. Acids Res., vol. 22, No. 20, 1994, pp. 4167-4175.

Pastinen et al., "A System for Specific, High-throughput Genotyping by Allele-specific Primer Extension on Microarrays", Genome Research, Cold Spring Harbor Laboratory Press, vol. 10, 2000, 1031-1042.

Pastinen et al., "Minisequencing: A Specific Tool for DNA Analysis and Diagnostics on Oligonucleotide Arrays", Genome Research, Cold Spring Harbor Laboratory, vol. 7, 1997, 606-614.

Richard, A. J. et al., "Thermal stability landscape for Klenow DNA polymerase as a function of pH and salt concentration," Biochemica et Biophysica Acta, 2006, vol. 1764, pp. 1546-1552.

Syvanen et al., "A Primer-Guided Nucleotide Incorporation Assay in the Genotyping of Apolipoprotein E", Genomics, 1990, 8(4):684-692.

Syvanen, "Accessing Genetic Variation: Genotyping Single Nucleotide Polymorphisms", Nature Reviews: Genetics, 2, 2001, 930-942.

Syvanen et al., "Detection of Point Mutations by Solid-Phase Methods", Human Mutation 3, 1994, 172-179.

\* cited by examiner

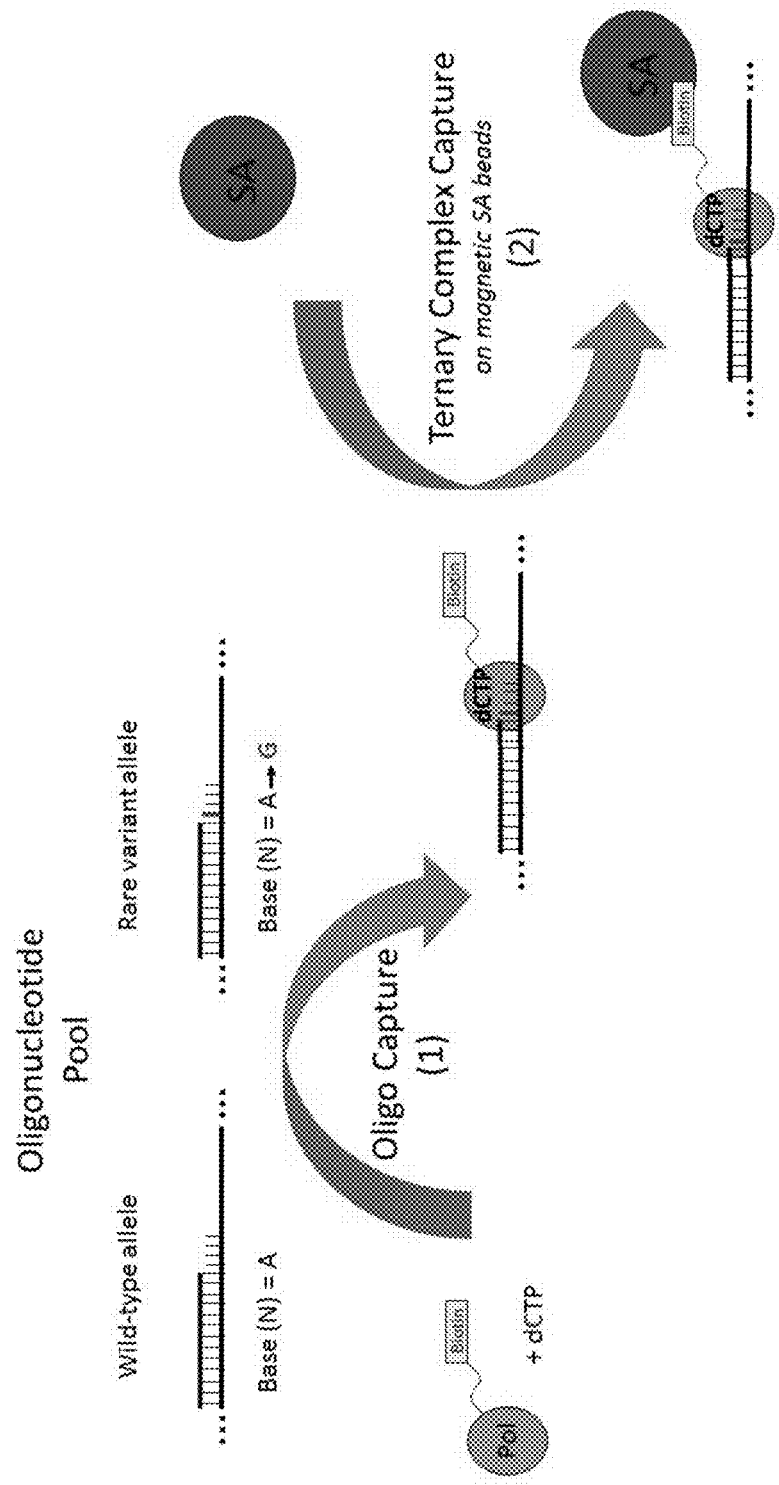

ALLELE-SPECIFIC CAPTURE OF NUCLEIC ACIDS

CROSS-REFERENCE TO RELATED APPLICATION

This application claims the benefit of U.S. Provisional Application No. 62/448,730, filed Jan. 20, 2017, which is hereby incorporated by reference in its entirety.

BACKGROUND

Small differences in nucleic acid sequences can result in significant differences in biological function. In the diagnostic context, single nucleotide polymorphisms (SNPs) in the human genome underlie differences in susceptibility to disease. A wide range of human diseases, such as sickle-cell anemia, β-thalassemia, Alzheimer's and cystic fibrosis result from SNPs.

In other contexts, single nucleotide mutations can be effective for gene therapy or synthetic biology. In gene therapy approaches a single nucleotide change can provide a healthy version of a gene that when introduced to a patient's cells will treat a disease that is caused by a mutant version of the gene. Synthetic biology can create industrially useful bio-molecules based on mutations, even at a single nucleotide site, in the nucleic acids that encode them.

The ability to capture or select a nucleic acid having a desired SNP or mutant is useful for characterization, synthesis, and quality assessment of nucleic acids in many contexts such as the diagnostic, therapeutic and synthetic approaches exemplified above. In many situations the desired sequences are in low abundance and/or present in a background of contaminants such as other nucleic acids having different sequences. Current methods exploit the specificity of binding between complementary nucleic acid strands for such capture and selection. In a typical technique, a target nucleic acid is captured using a support-bound nucleic acid that is complementary to the sequence of the target nucleic acid. Although, complementarity is theoretically capable of distinguishing sequences, in practical terms many samples are highly complex with regard to the variety of non-target sequences present and with regard to the sheer number of non-target molecules compared to target molecule. Such complexity makes it impractical and in some cases improbable to selectively capture a sequence that differs from contaminating nucleic acids by only one or a few nucleotides.

Thus, there exists a need for methods to separate nucleic acids that differ from each other by only a few or even only one nucleotide. The present disclosure satisfies this need and provides related advantages as well.

BRIEF SUMMARY

The present disclosure provides a method for separating a target allele from a mixture of nucleic acids. The method can include steps of (a) providing a mixture of nucleic acids in fluidic contact with a stabilized ternary complex that is attached to a solid support, wherein the stabilized ternary complex includes a polymerase, primed nucleic acid template, and next correct nucleotide, wherein the template has a target allele, wherein the next correct nucleotide is a cognate nucleotide for the target allele, and wherein the stabilized ternary complex is attached to the solid support via a linkage between the polymerase and the solid support or via a linkage between the nucleotide and the solid support; and (b) separating the solid support from the mixture of nucleic acids, thereby separating the target allele from the mixture of nucleic acids.

Also provided is a method for separating a first allele of a locus from a second allele at the locus. The method can include steps of (a) providing a mixture including the second allele in fluidic contact with a stabilized ternary complex that is attached to a solid support, wherein the stabilized ternary complex includes a polymerase, primer hybridized to a nucleic acid template, and next correct nucleotide, wherein the template has the first allele, wherein the next correct nucleotide is a cognate nucleotide for the first allele or the 3' end of the primer has a cognate nucleotide for the first allele, and wherein the stabilized ternary complex is attached to the solid support via a linkage between the polymerase and the solid support or via a linkage between the next correct nucleotide and the solid support; and (b) separating the solid support from the mixture of nucleic acids, thereby separating the first allele from the second allele.

This disclosure further provides a method for separating a plurality of target alleles from a mixture of nucleic acids. The method can include steps of (a) providing a mixture of nucleic acids in fluidic contact with a plurality of stabilized ternary complexes that are solid support-attached, wherein the stabilized ternary complexes each includes a polymerase, primed nucleic acid template, and next correct nucleotide, wherein the template has a target allele, wherein the next correct nucleotide is a cognate nucleotide for the target allele, and wherein each of the stabilized ternary complexes is attached to the solid support via a linkage between the polymerase and the solid support or via a linkage between the next correct nucleotide and the solid support; and (b) separating the solid support from the mixture of nucleic acids, thereby separating the target alleles from the mixture of nucleic acids.

The disclosure further provides a method for separating first alleles at a plurality of loci from second alleles at the plurality of loci, respectively. The method can include steps of (a) providing a mixture of the second alleles at the plurality of loci, respectively, in fluidic contact with a plurality of stabilized ternary complexes that are solid support-attached, wherein the stabilized ternary complexes each include a polymerase, primed nucleic acid template, and next correct nucleotide, wherein the template includes a first allele, wherein the next correct nucleotide is a cognate nucleotide for the first allele or the 3' end of the primer includes a cognate nucleotide for the first allele, and wherein each of the stabilized ternary complexes is attached to the solid support via a linkage between the polymerase and the solid support or via a linkage between the next correct nucleotide and the solid support; and (b) separating the solid support from the mixture of nucleic acids, thereby separating the first alleles from the second alleles at the plurality of loci.

BRIEF DESCRIPTION OF THE DRAWINGS

FIG. 2 is a schematic showing a diagrammatic representation for a method of separating a rare variant allele from a wild type allele that includes a step (1) of capturing the rare allele by formation of a stabilized ternary complex with a cognate nucleotide and a biotinylated polymerase, followed by a step (2) of binding the biotinylated polymerase to a streptavidin coated bead to separate the allele-bearing ternary complex from the wild type allele.

DETAILED DESCRIPTION

The present disclosure provides polymerase-based methods for selecting or capturing nucleic acids having target alleles of interest. Embodiments of the methods exploit the specificity with which a polymerase can form a stabilized ternary complex with a primed template and a next correct nucleotide. For example, a stabilized ternary complex can be formed between a polymerase, target allele and cognate nucleotide for the allele. An advantage of the methods is that polymerase specificity allows a target allele to be separated from other nucleic acids, including for example, other alleles that differ from the target allele by a single nucleotide. For example, a ternary complex can be formed between a polymerase, a primed template encoding a target single nucleotide polymorphism (SNP) allele and a cognate nucleotide for the SNP allele. Capture of the ternary complex will result in selective capture of the SNP allele, compared to a non-target SNP allele at the same locus, because the cognate nucleotide is selective for the target SNP when forming a ternary complex with the polymerase.

Figure 1A:
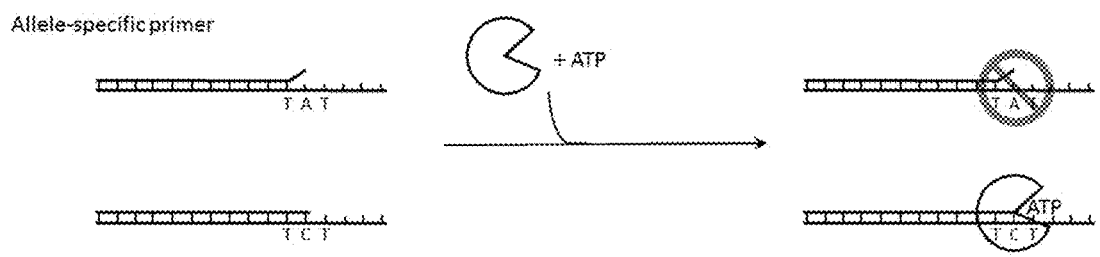
FIG. 1A is a schematic showing a diagrammatic representation for allele-specific ternary complex formation using a polymerase (represented as a pie shape), allele-specific primer bound to a template, and cognate nucleotide that binds at a position on the template that is adjacent to the allele position.

Methods and compositions set forth herein can be used to capture and optionally enrich rare alleles (e.g. DNA- or RNA-based) containing various mutations within their sequences. The methods are well suited to capture even rare variant alleles from pools of purified or semi-purified oligonucleotides containing wild-type DNA sequences of the same locus, as well as other unrelated sequences. FIG. 1 shows diagrammatic representations for two different primer-nucleotide combinations that can be used to form allele-specific ternary complexes. As shown in FIG. 1A an allele-specific primer can be used such that the 3' end of the primer is selectively matched to a target allele at a specific locus, but mismatched to other alleles at the locus. For example, in the case of a single nucleotide polymorphism (SNP) locus the 3' end of the primer base-pairs with the targeted SNP allele C at position N, but not with allele A at position N. Upon addition of a polymerase and next correct nucleotide for position N+1 (i.e. ATP in the Figure) a stabilized ternary complex can be formed selectively for the target allele, under conditions that do not form stabilized ternary complex with the mismatched, non-target allele.

Figure 1B:
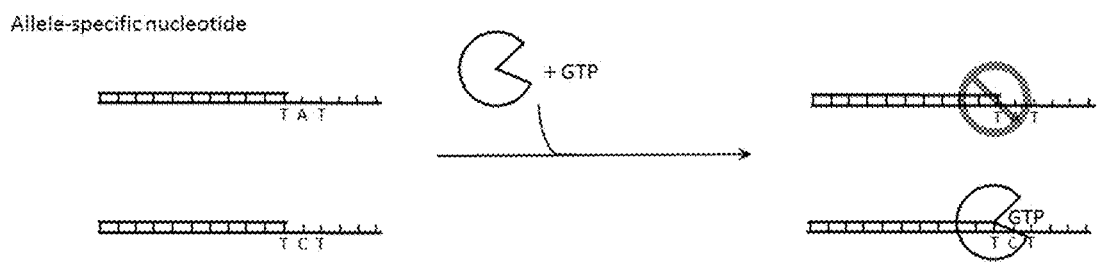
FIG. 1B is a schematic showing a diagrammatic representation for allele-specific ternary complex formation using a polymerase (represented as a pie shape), allele-specific cognate nucleotide and a locus primer that binds at a region adjacent to the allele position.

Alternatively, as shown in FIG. 1B, a locus primer can be used that binds to multiple alleles of a particular locus, such that the 3' end of the locus primer base-pairs with N−1 position. This configuration leaves the target base of interest (at position N) available for binding to an allele specific cognate nucleotide. Again taking the example of a SNP locus, the primer hybridizes to both alleles. Upon addition of a polymerase and the cognate nucleotide for the target SNP (i.e. the target SNP being C and the cognate nucleotide being GTP in the Figure), a stabilized ternary complex can be formed selectively for the target allele, under conditions that do not form stabilized ternary complex with the non-target, A allele.

Figure 3:
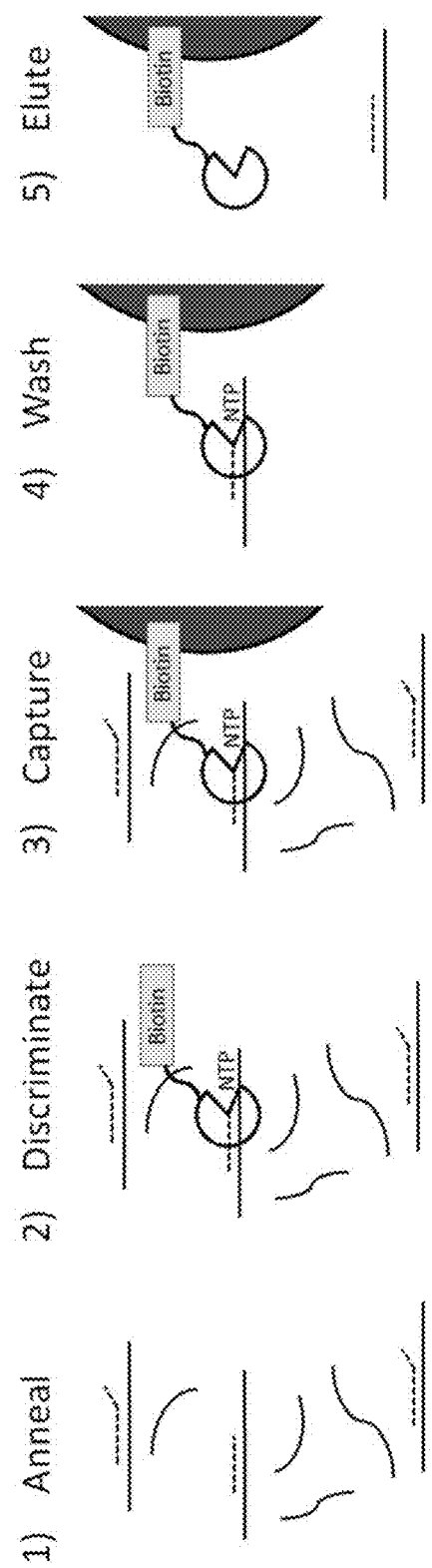
FIG. 3 is a schematic showing an exemplary workflow for separating a rare variant allele from a wild type allele that includes steps of (1) annealing specific capture primer(s) (dotted lines) to a sample containing a mixture of nucleic acids composed of the desired target(s) as well as off-target species (solid lines); (2) adding a polymerase (pie-shape) containing a covalently attached biotin in the presence of a non-catalytic metal and cognate dNTP; (3) adding a solid capture support (partial arc of solid circle coated with streptavidin; (4) washing captured ternary complexes under discriminating conditions in the presence of the non-catalytic metal and the dNTP; and (5) Eluting the targeted nucleic acid, for example, by adding a molar excess of Mg' ions or dissociating the complex.

FIG. 2 shows a diagrammatic representation for allele-specific ternary complex formation using a locus primer and allele-specific cognate nucleotide followed by capture of the ternary complex. The binding of a biotinylated polymerase in the presence of the correct dNTP (dCTP in the Figure) under ternary complex stabilizing conditions, will generate a capturable ternary complex with significant preference for the rare allele. The biotinylated ternary complex can be captured on magnetic streptavidin beads having affinity for the biotinylated polymerase. The beads and fluidic components can be separated to remove the ternary complex from contaminants including nucleic acids having the wild-type allele. Optionally the beads can be washed, in the presence of the same dNTP used for capture of the rare variant allele, to further remove contaminants. Gentle elution of the nucleic acid having the rare variant allele can be achieved by contacting the ternary complex with Mg' or other ternary complex destabilizing conditions, without polymerase and without dNTP. The enriched allele can then be used in a variety of desired applications including, for example, amplification, synthetic procedures or analytic procedures such as sequencing. Although FIG. 2 is exemplified using an allele-specific nucleotide format (e.g. as shown in FIG. 1B), it will be understood that an allele-specific primer format can be used as well (e.g. as shown in FIG. 1A). An exemplary workflow for a method using allele-specific primer is shown in FIG. 3.

Generally, the methods set forth herein allow for separation of alleles. As demonstrated by the Example of FIG. 2, separation can be carried out to result in enrichment of a target allele. However, it will be understood that separation can be carried out to result in depletion of a target allele. More specifically, the method shown in FIG. 2 can be modified to capture the wild-type allele by forming a biotinylated ternary complex in the presence of dTTP instead of dCTP. Depletion of the wild-type allele in this way can leave behind a more enriched population of rare variant alleles. Accordingly, it will be understood that the term "target allele" can be used herein to refer to an allele that is targeted for ternary complex formation in a method set forth herein independent of the desirability for using the captured allele afterward. Thus, a target allele can be captured for purposes of enriching the captured target allele for subsequent use or, alternatively, the target allele can be captured for purposes of being subsequently discarded.

It will be understood that a particular allele can be obtained using a combination of depletion and enrichment methods. For example, a rare variant allele can be separated from a more prominent wild type allele by subjecting a genomic sample that bears the alleles to the following iterations. First a method set forth herein can be used to deplete the wild-type allele from the genomic sample (i.e. by forming a ternary complex that targets the wild type allele and then removing this ternary complex from the sample) and then subjecting the sample to a method set forth herein to enrich for the rare variant allele (i.e. by forming a ternary complex that targets the rare variant allele and then removing this ternary complex from the sample). In this example, depletion is carried out prior to enrichment, but the order can be reversed if desired. Furthermore, the methods can be multiplexed to process a plurality of alleles in parallel.

Terms used herein will be understood to take on their ordinary meaning in the relevant art unless specified otherwise. Several terms used herein and their meanings are set forth below.

As used herein, the term "allele," when used in reference to a genetic locus, refers to any of the alternative nucleotides, sequences or other genetic features that occur at the genetic locus. Exemplary alleles include, but are not limited to single nucleotide polymorphisms (SNPs), insertions and/or deletions (indels), alternative mRNA splice sites or repeats that occur at a locus.

As used herein, the term "allele-specific primer" refers to an oligonucleotide that is complementary to one allele of a locus and not to another allele of the locus. A portion of an allele-specific primer can be complementary to both alleles, so long as at least one nucleotide in the primer is a cognate for only one of the alleles. For example, an allele-specific primer can have a 3' nucleotide that is a cognate of a first allele at a locus, but not a cognate of a second allele at the locus. It will be understood that an allele-specific primer can have a portion, for example, a tag or linker, that lacks complementarity to either allele.

As used herein, the term "array" refers to a population of molecules that are attached to one or more solid-phase substrates such that the molecules at one feature can be distinguished from molecules at other features. An array can include different molecules that are each located at different addressable features on a solid-phase substrate. Alternatively, an array can include separate solid-phase substrates each functioning as a feature bearing a different molecule, wherein the different probe molecules can be identified according to the locations of the solid-phase substrates on a surface to which the solid-phase substrates are attached or according to the locations of the solid-phase substrates in a liquid such as a fluid stream. The molecules of the array can be nucleotides, nucleic acid primers, nucleic acid probes, nucleic acid templates or nucleic acid enzymes such as polymerases, ligases or exonucleases.

As used herein, the term "catalytic metal ion" refers to a metal ion that facilitates phosphodiester bond formation between the 3'-OH of a nucleic acid (e.g., a primer) and the phosphate of an incoming nucleotide by a polymerase. A "divalent catalytic metal cation" is a catalytic metal ion having a valence of two. Catalytic metal ions can be present at concentrations that stabilize formation of a complex between a polymerase, nucleotide, and primed template nucleic acid, referred to as non-catalytic concentrations of a metal ion insofar as phosphodiester bond formation does not occur. Catalytic concentrations of a metal ion refer to the amount of a metal ion sufficient for polymerases to catalyze the reaction between the 3'-OH group of a nucleic acid (e.g., a primer) and the phosphate group of an incoming nucleotide.

As used herein, the term "comprising" is intended to be open-ended, including not only the recited elements, but further encompassing any additional elements.

As used herein, the term "each," when used in reference to a collection of items, is intended to identify an individual item in the collection but does not necessarily refer to every item in the collection. Exceptions can occur if explicit disclosure or context clearly dictates otherwise.

As used herein, the term "exogenous," when used in reference to a moiety of a molecule, means a chemical moiety that is not present in a natural analog of the molecule. For example, an exogenous label of a nucleotide is a label that is not present on a naturally occurring nucleotide. Similarly, an exogenous label that is present on a polymerase is not found on the polymerase in its native milieu.

As used herein, the term "extension," when used in reference to a nucleic acid, refers to a process of adding at least one nucleotide to the 3' end of the nucleic acid. A nucleotide that is added to a nucleic acid by extension is said to be incorporated into the nucleic acid. Accordingly, the term "incorporating" can be used to refer to the process of joining a nucleotide to the 3' end of a nucleic acid by formation of a phosphodiester bond.

As used herein, the term "feature" means a location in an array where a particular molecule is present. A feature can contain only a single molecule or it can contain a population of several molecules of the same species. Alternatively, a feature can include a population of molecules that are different species (e.g. a population of ternary complexes having different template sequences). Features of an array are typically discrete. The discrete features can be contiguous or they can have spaces between each other. An array useful herein can have, for example, features that are separated by less than 100 micron, 50 micron, 10 micron, 5 micron, 1 micron, or 0.5 micron. Alternatively or additionally, an array can have features that are separated by greater than 0.5 micron, 1 micron, 5 micron, 10 micron, 50 micron or 100 micron. The features can each have an area of less than 1 square millimeter, 500 square micron, 100 square micron, 25 square micron, 1 square micron or less.

As used herein, the term "gel material" is intended to mean a semi-rigid material that is permeable to liquids and gases. Typically, gel material can swell when liquid is taken up and can contract when liquid is removed by drying. Exemplary gels include, but are not limited to those having a colloidal structure, such as agarose; polymer mesh structure, such as gelatin; or cross-linked polymer structure, such as polyacrylamide. Useful gels are described, for example, in US Pat. App. Pub. No. 2011/0059865 A1, and U.S. Pat. No. 9,012,022, each of which is incorporated herein by reference.

The term "locus," when used in reference to a nucleic acid, refers to the position in the nucleic acid where a nucleotide, nucleic acid sequence or other genetic feature occurs.

As used herein, the term "locus-specific primer" refers to an oligonucleotide that is complementary to a first locus in a nucleic acid and not to a second locus in the nucleic acid, wherein at least two alleles of the first locus are complementarity to the oligonucleotide. For example, the locus-specific primer can be complementary to a portion of the locus that is near or adjacent to the position of the two alleles in the nucleic acid. In the latter configuration, a locus-specific primer can hybridize to the nucleic acid adjacent to a next template nucleotide that is an allele. It will be understood that a locus-specific primer can have a portion, for example, a tag portion or linker, that lacks complementarity to either locus.

As used herein, the term "next correct nucleotide" refers to the nucleotide type that will bind and/or incorporate at the 3' end of a primer to complement a base in a template strand to which the primer is hybridized. The base in the template strand is referred to as the "next template nucleotide" and is immediately 5' of the base in the template that is hybridized to the 3' end of the primer. The next correct nucleotide can be referred to as the "cognate" of the next template nucleotide and vice versa. Cognate nucleotides that interact with each other in a ternary complex or in a double stranded nucleic acid are said to "pair" with each other. A nucleotide having a base that is not complementary to the next template base is referred to as an "incorrect", "mismatch" or "non-cognate" nucleotide.

As used herein, the term "non-catalytic metal ion" refers to a metal ion that, when in the presence of a polymerase enzyme, does not facilitate phosphodiester bond formation needed for chemical incorporation of a nucleotide into a primer. A non-catalytic metal ion may interact with a polymerase, for example, via competitive binding compared to catalytic metal ions. A "divalent non-catalytic metal ion" is a non-catalytic metal ion having a valence of two. Examples of divalent non-catalytic metal ions include, but are not limited to, $Ca^{2+}$, $Zn^{2+}$, $Co^{2+}$, $Ni^{2+}$, and $Sr^{2+}$. The trivalent $Eu^{3+}$ and $Tb^{3+}$ ions are non-catalytic metal ions having a valence of three.

As used herein, the term "polymerase" can be used to refer to a nucleic acid synthesizing enzyme, including but not limited to, DNA polymerase, RNA polymerase, reverse transcriptase, primase and transferase. Typically, the polymerase comprises one or more active sites at which nucleotide binding and/or catalysis of nucleotide polymerization may occur. The polymerase may catalyze the polymerization of nucleotides to the 3' end of the first strand of the double stranded nucleic acid molecule. For example, a polymerase catalyzes the addition of a next correct nucleotide to the 3' OH group of the first strand of the double stranded nucleic acid molecule via a phosphodiester bond, thereby covalently incorporating the nucleotide to the first strand of the double stranded nucleic acid molecule. Optionally, a polymerase need not be capable of nucleotide incorporation under one or more conditions used in a method set forth herein. For example, a mutant polymerase may be capable of forming a ternary complex but incapable of catalyzing nucleotide incorporation.

As used herein, the term "solid support" refers to a rigid substrate that is insoluble in aqueous liquid. The substrate can be non-porous or porous. The substrate can optionally be capable of taking up a liquid (e.g. due to porosity) but will typically be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers.

As used herein, the term "ternary complex" refers to an intermolecular association between a polymerase, a double stranded nucleic acid and a nucleotide. Typically, the polymerase facilitates interaction between a next correct nucleotide and a template strand of the primed nucleic acid. A next correct nucleotide can interact with the template strand via Watson-Crick hydrogen bonding. The term "stabilized ternary complex" means a ternary complex having promoted or prolonged existence or a ternary complex for which disruption has been inhibited. Generally, stabilization of the ternary complex prevents incorporation of the nucleotide component of the ternary complex into the primed nucleic acid component of the ternary complex.

The embodiments set forth below and recited in the claims can be understood in view of the above definitions.

The present disclosure provides a method for separating a target allele from a mixture of nucleic acids. The method can include steps of (a) providing a mixture of nucleic acids in fluidic contact with a stabilized ternary complex that is attached to a solid support, wherein the stabilized ternary complex includes a polymerase, primed nucleic acid template, and next correct nucleotide, wherein the template has a target allele, wherein the next correct nucleotide is a cognate nucleotide for the target allele, and wherein the stabilized ternary complex is attached to the solid support via a linkage between the polymerase and the solid support or via a linkage between the nucleotide and the solid support; and (b) separating the solid support from the mixture of nucleic acids, thereby separating the target allele from the mixture of nucleic acids.

Also provided is a method for separating a first allele of a locus from a second allele at the locus. The method can include steps of (a) providing a mixture including the second allele in fluidic contact with a stabilized ternary complex that is attached to a solid support, wherein the stabilized ternary complex includes a polymerase, primer hybridized to a nucleic acid template, and next correct nucleotide, wherein the template has the first allele, wherein the next correct nucleotide is a cognate nucleotide for the first allele or the 3' end of the primer has a cognate nucleotide for the first allele, and wherein the stabilized ternary complex is attached to the solid support via a linkage between the polymerase and the solid support or via a linkage between the next correct nucleotide and the solid support; and (b) separating the solid support from the mixture of nucleic acids, thereby separating the first allele from the second allele.

Described herein are polymerase-based methods for capturing nucleic acids having target sequences of interest such as target alleles. Embodiments of the methods exploit the specificity with which a polymerase can form a stabilized ternary complex with the target allele and a cognate nucleotide for the allele. The stabilized ternary complex can include the polymerase, a primed nucleic acid template having the target allele, and a cognate nucleotide for the target allele. The cognate nucleotide is not covalently attached to the primer in the stabilized ternary complex, instead being bound to the complex by non-covalent interactions. In particular embodiments, the cognate nucleotide is non-covalently bound to the stabilized ternary complex, interacting with the other members of the complex solely via non-covalent interactions. Useful methods and compositions for forming a ternary complex are set forth in further detail below and in commonly owned U.S. Ser. No. 14/805,381, now published as U.S. Publication No. 2017/0022553 A1, and 62/375,379, which is incorporated by reference in U.S. Ser. No. 15/677,870, each of which is incorporated herein by reference.

While a ternary complex can form between a polymerase, primed template nucleic acid and next correct nucleotide in the absence of certain catalytic metal ions (e.g., $Mg^{2+}$), chemical addition of the nucleotide is inhibited in the absence of the catalytic metal ions. Low or deficient levels of catalytic metal ions, causes non-covalent (physical) sequestration of the next correct nucleotide in a stabilized ternary complex. Other methods disclosed herein also can be used to produce a stabilized ternary complex.

Optionally, a stabilized ternary complex can be formed when the primer of the primed template nucleic acid includes a blocking group that precludes enzymatic incorporation of an incoming nucleotide into the primer. The interaction can take place in the presence of stabilizers, whereby the polymerase-nucleic acid interaction is stabilized in the presence of the next correct nucleotide (i.e., stabilizers that stabilize the ternary complex). The primer of the primed template nucleic acid optionally can be either an extendible primer, or a primer blocked from extension at its 3'-end (e.g., by the presence of a reversible terminator moiety). The primed template nucleic acid, the polymerase and the cognate nucleotide are capable of forming a ternary complex when the base of the cognate nucleotide is complementary to the next base of the primed template nucleic acid.

As set forth above, conditions that favor or stabilize a ternary complex can be provided by the presence of a blocking group that precludes enzymatic incorporation of an incoming nucleotide into the primer (e.g. a reversible terminator moiety on the 3' nucleotide of the primer) or the absence of a catalytic metal ion. Other useful conditions include the presence of a ternary complex stabilizing agent such as a non-catalytic ion (e.g., a divalent or trivalent non-catalytic metal ion) that inhibits nucleotide incorporation or polymerization. Metal ions that can be used as non-catalytic metal ions for particular polymerases include, but are not limited to, calcium, strontium, scandium, titanium, vanadium, chromium, iron, cobalt, nickel, copper, zinc, gallium, germanium, arsenic, selenium, rhodium, europium, and terbium ions. Optionally, conditions that disfavor or destabilize binary complexes (i.e. complexes between polymerase and primed nucleic acid but lacking cognate nucleotide) are provided by the presence of one or more monovalent cations and/or glutamate anions. As a further option, a polymerase engineered to have reduced catalytic activity or reduced propensity for binary complex formation can be used. Another option, is the use of non-incorporable or non-hydrolyzable nucleotides that can form a discriminating ternary complex but cannot be incorporated into the primer strand.

As set forth above, ternary complex stabilization conditions can accentuate the difference in affinity of polymerase toward primed template nucleic acids in the presence of different nucleotides, for example, by destabilizing binary complexes. Optionally, the conditions cause differential affinity of the polymerase for the primed template nucleic acid in the presence of different nucleotides. By way of example, the conditions include, but are not limited to, high salt and glutamate ions. For example, the salt may dissolve in aqueous solution to yield a monovalent cation, such as a monovalent metal cation (e.g., sodium ion or potassium ion). Optionally, the salt that provides the monovalent cations (e.g., monovalent metal cations) further provides glutamate anions. Optionally, the source of glutamate ions can be potassium glutamate. In some instances, the concentrations of potassium glutamate that can be used to alter polymerase affinity of the primed template nucleic acid extend from 10 mM to 1.6 M of potassium glutamate, or any amount in between 10 mM and 1.6 M. As indicated above, high salt refers to a concentration of salt from 50 to 1,500 mM salt.

It will be understood that options set forth herein for stabilizing a ternary complex need not be mutually exclusive and instead can be used in various combinations. For example, a ternary complex can be stabilized by one or a combination of means including, but not limited to, cross-linking of the polymerase domains, crosslinking of the polymerase to the nucleic acid, polymerase mutations that stabilize the ternary complex, allosteric inhibition by small molecules, uncompetitive inhibitors, competitive inhibitors, non-competitive inhibitors, and other means set forth herein.

A ternary complex that is made or used in accordance with the present disclosure may optionally include one or more exogenous label. The label can be present on the polymerase, template nucleic acid, primer and/or cognate nucleotide. Exogenous labels can be useful for detecting a ternary complex or an individual component thereof, during one or more of the manipulations set forth herein. Exemplary labels, methods for attaching labels and methods for using labeled components are set forth in commonly owned U.S. Ser. No. 14/805,381, now published as U.S. Publication No. 2017/0022553, and 62/375,379, which is incorporated by reference in U.S. Ser. No. 15/677,870, each of which is incorporated herein by reference.

In alternative embodiments, a ternary complex can lack exogenous labels. For example, a ternary complex and components used in the formation of the ternary complex (e.g. polymerase, template nucleic acid, primer and/or cognate nucleotide) can lack one, several or all of the exogenous labels described in the above-incorporated references.

A ternary complex can be formed with any of a variety of nucleic acid template sequences in a method set forth herein. The methods are particularly useful for selectively capturing one allele at a genetic locus to separate it from one or more other alleles at the locus. Thus, a mixture of nucleic acid templates that is used in a method set forth herein can include first and second alleles at a particular locus, one of which is selectively captured. The mixture can include a variety of other nucleic acids, for example, some or all of the sequence content of a genome or exome from one or more organism.

Methods set forth herein can be particularly useful for selectively capturing a minor allele. The minor allele can be one of a pair occurring at bi-allelic locus, one of three alleles at a tri-allelic locus or one of four alleles at a quad-allelic locus. The minor allele frequency of an allele captured herein can be at most 40%, 25%, 10%, 5%, 0.5% or less. The methods can also be used to capture alleles having higher frequency including, for example, major alleles. Exemplary alleles that can be captured include, without limitation, single nucleotide polymorphisms (SNPs), insertion-deletion (indel) polymorphisms and alternative splicing polymorphisms.

Although the methods of the present disclosure are particularly well suited to selectively capturing an allele at a multi-allelic locus, other sequences can also be captured. Thus, the methods and compositions exemplified for alleles can be extended to other sequences and other templates. For example, the methods can be used to capture a non-polymorphic sequence. In such cases the next correct nucleotide and primer need not correlate to a particular allele in the template. In other embodiments, the methods can be used to selectively capture a mutant sequence compared to its wild-type sequence or vice versa. This can be useful for example, when manipulating or evaluating reagents for or products of protein engineering or synthetic biology.

Nucleic acid templates that are used in a method or composition herein can be DNA such as genomic DNA, synthetic DNA, amplified DNA, complementary DNA (cDNA) or the like. RNA can also be used such as mRNA, ribosomal RNA, tRNA or the like. Nucleic acid analogs can also be used as templates herein. Thus, a mixture of nucleic acids used herein can be derived from a biological source, synthetic source or amplification product. Primers used herein can be DNA, RNA or analogs thereof.

Exemplary organisms from which nucleic acids can be derived include, for example, those from a mammal such as a rodent, mouse, rat, rabbit, guinea pig, ungulate, horse, sheep, pig, goat, cow, cat, dog, primate, human or non-human primate; a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a *dictyostelium discoideum*; a fungi such as *pneumocystis carinii, Takifugu rubripes*, yeast, *Saccharamoyces cerevisiae* or *Schizosaccharomyces pombe*; or a *plasmodium falciparum*. Nucleic acids can also be derived from a prokaryote such as a bacterium, *Escherichia coli, staphylococci* or *mycoplasma pneumoniae*; an archae; a virus such as Hepatitis C virus or human immunodeficiency virus; or a viroid. Nucleic acids can be derived from a homogeneous culture or population of the above organisms or alternatively from a collection of several different organisms, for example, in a community or ecosystem. Nucleic acids can be isolated using methods known in the art including, for example, those described in Sambrook et al., *Molecular Cloning: A Laboratory Manual*, 3rd edition, Cold Spring Harbor Laboratory, New York (2001) or in Ausubel et al., *Current Protocols in Molecular Biology*, John Wiley and Sons, Baltimore, Md. (1998), each of which is incorporated herein by reference.

Particular embodiments of the methods set forth herein can use a native nucleotide, nucleotide analog or modified nucleotide. Such nucleotides can be used, for example, for forming a stabilized ternary complex. Optionally, a nucleotide analog comprises a nitrogenous base, five-carbon sugar, and phosphate group; wherein any moiety of the nucleotide may be modified, removed and/or replaced. Nucleotide analogs may be non-incorporable nucleotides. Such nucleotides incapable of incorporation include, for example, monophosphate and diphosphate nucleotides. In another example, the nucleotide may contain modification(s) to the triphosphate group that make the nucleotide non-incorporable. Examples of non-incorporable nucleotides may be found in U.S. Pat. No. 7,482,120, which is incorporated by reference herein. Non-incorporable nucleotides may be subsequently modified to become incorporable. Nucleotide analogs include, but are not limited to, alpha-phosphate modified nucleotides, alpha-beta nucleotide analogs, beta-phosphate modified nucleotides, beta-gamma nucleotide analogs, gamma-phosphate modified nucleotides, caged nucleotides, or ddNTPs. Examples of nucleotide analogs are described in U.S. Pat. No. 8,071,755, which is incorporated by reference herein.

Nucleotide analogs can include terminators that reversibly prevent nucleotide incorporation at the 3'-end of the primer after the analog has been incorporated. For example, U.S. Pat. No. 7,544,794 and U.S. Pat. No. 8,034,923 (the disclosures of these patents are incorporated herein by reference) describe reversible terminators in which the 3'-OH group is replaced by a 3'-ONH$_2$ moiety. Another type of reversible terminator is linked to the nitrogenous base of a nucleotide as set forth, for example, in U.S. Pat. No. 8,808,989 (the disclosure of which is incorporated herein by reference). Other reversible terminators that similarly can be used in connection with the methods described herein include those described in U.S. Pat. No. 7,956,171, U.S. Pat. No. 8,071,755, and U.S. Pat. No. 9,399,798 (the disclosures of these U.S. patents are incorporated herein by reference). In certain embodiments, a reversible blocking moiety can be removed from a primer, allowing for nucleotide incorporation. Compositions and methods for deblocking are set forth in the above references.

Alternatively, nucleotide analogs irreversibly prevent nucleotide incorporation at the 3'-end of the primer to which they have been incorporated. Irreversible nucleotide analogs include 2', 3'-dideoxynucleotides, ddNTPs (ddGTP, ddATP, ddTTP, ddCTP). Dideoxynucleotides lack the 3'-OH group of dNTPs that is essential for polymerase-mediated primer extension.

Optionally, a nucleotide (e.g. a native nucleotide or nucleotide analog) is present in a mixture during formation of a stabilized ternary complex. For example, at least 1, 2, 3, 4 or more nucleotide types can be present. Alternatively or additionally, at most 4, 3, 2, or 1 nucleotide types can be present. Similarly, one or more nucleotide types that are present can be complementary to at least 1, 2, 3 or 4 nucleotide types in a template nucleic acid. Alternatively or additionally, one or more nucleotide types that are present can be complementary to at most 4, 3, 2, or 1 nucleotide types in a template nucleic acid.

Optionally, a nucleotide analog is fused to a polymerase. Optionally, a plurality of nucleotide analogs comprises fusions to a plurality of polymerases, wherein each nucleotide analog comprises a different polymerase.

Any nucleotide modification that stabilizes a polymerase in a ternary complex may be used in the methods disclosed herein. The nucleotide may be bound permanently or transiently. Optionally, a nucleotide that is present in a stabilized ternary complex is not the means by which the ternary complex is stabilized. Accordingly, any of a variety of other ternary complex stabilization methods may be combined in a reaction utilizing a nucleotide analog.

In particular embodiments, the primer strand of a primed template nucleic acid molecule undergoing one or more steps of a method set forth herein is chemically unchanged by the polymerase. This is to say that the primer is neither extended by formation of a new phosphodiester bond, nor shortened by nucleolytic degradation during the examination step to identify the next correct nucleotide.

Polymerases that may be used to carry out a method of the present disclosure include naturally occurring polymerases and modified variations thereof, including, but not limited to, mutants, recombinants, fusions, genetic modifications, chemical modifications, synthetics, and analogs. Naturally occurring polymerases and modified variations thereof are not limited to polymerases that retain the ability to catalyze a polymerization reaction. Optionally, the naturally occurring and/or modified variations thereof retain the ability to catalyze a polymerization reaction. Optionally, the naturally-occurring and/or modified variations have special properties, for example, enhanced binding affinity to nucleic acids, reduced binding affinity to nucleic acids, enhanced binding affinity to nucleotides, reduced binding affinity to nucleotides, enhanced specificity for next correct nucleotides, reduced specificity for next correct nucleotides, enhanced catalysis rates, reduced catalysis rates, catalytic inactivity etc. Mutant polymerases include polymerases wherein one or more amino acids are replaced with other amino acids, and insertions or deletions of one or more amino acids.

Modified polymerases include polymerases that contain an exogenous affinity moiety (e.g., an exogenous ligand or receptor), which can be used to capture or manipulate the polymerase. Optionally, the affinity moiety can be attached after the polymerase has been at least partially purified using protein isolation techniques. For example, the exogenous affinity moiety can be chemically linked to the polymerase using a free sulfhydryl or a free amine moiety of the polymerase. This can involve chemical linkage to the polymerase through the side chain of a cysteine residue, or through the free amino group of the N-terminus. An exogenous affinity moiety can also be attached to a polymerase via protein fusion. Exemplary affinity moiety that can be attached via protein fusion include, for example, poly histidine, antibody fragments, epitopes for particular antibodies, streptavidin and affinity tags used for purification of recombinant proteins (e.g. commercially available affinity tags from ThermoFisher, Waltham, Mass. or Promega, Madison Wis.).

Useful DNA polymerases include, but are not limited to, bacterial DNA polymerases, eukaryotic DNA polymerases, archaeal DNA polymerases, viral DNA polymerases and phage DNA polymerases. Bacterial DNA polymerases include *E. coli* DNA polymerases I, II and III, IV and V, the Klenow fragment of *E. coli* DNA polymerase, *Clostridium stercorarium* (Cst) DNA polymerase, *Clostridium thermocellum* (Cth) DNA polymerase and *Sulfolobus solfataricus* (Sso) DNA polymerase. Eukaryotic DNA polymerases include DNA polymerases α, β, γ, δ, €, η, ζ, λ, σ, μ, and k, as well as the Rev1 polymerase (terminal deoxycytidyl transferase) and terminal deoxynucleotidyl transferase (TdT). Viral DNA polymerases include T4 DNA polymerase, phi-29 DNA polymerase, GA-1, phi-29-like DNA polymerases, PZA DNA polymerase, phi-15 DNA polymerase, Cp1 DNA polymerase, Cp7 DNA polymerase, T7 DNA polymerase, and T4 polymerase. Other useful DNA polymerases include thermostable and/or thermophilic DNA polymerases such as *Thermus aquaticus* (Taq) DNA polymerase, *Thermus filiformis* (Tfi) DNA polymerase, *Thermococcus zilligi* (Tzi) DNA polymerase, *Thermus thermophilus* (Tth) DNA polymerase, *Thermus flavusu* (Tfl) DNA polymerase, *Pyrococcus woesei* (Pwo) DNA polymerase, *Pyrococcus furiosus* (Pfu) DNA polymerase and Turbo Pfu DNA polymerase, *Thermococcus litoralis* (Tli) DNA polymerase, *Pyrococcus* sp. GB-D polymerase, *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilium* DNA polymerase; *Sulfolobus acidocaldarius* DNA polymerase; *Thermococcus* sp. go N-7 DNA polymerase; *Pyrodictium occultum* DNA polymerase; *Methanococcus voltae* DNA polymerase; *Methanococcus thermoautotrophicum* DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pernix* DNA polymerase; and the heterodimeric DNA polymerase DP1/DP2. Engineered and modified polymerases also are useful in connection with the disclosed techniques. For example, modified versions of the extremely thermophilic marine archaea *Thermococcus* species 9° N (e.g., Therminator DNA polymerase from New England BioLabs Inc.; Ipswich, Mass.) can be used. Still other useful DNA polymerases, including the 3PDX polymerase are disclosed in U.S. Pat. No. 8,703,461, the disclosure of which is incorporated herein by reference.

Useful RNA polymerases include, but are not limited to, viral RNA polymerases such as T7 RNA polymerase, T3 polymerase, SP6 polymerase, and Kll polymerase; Eukaryotic RNA polymerases such as RNA polymerase I, RNA polymerase II, RNA polymerase III, RNA polymerase IV, and RNA polymerase V; and Archaea RNA polymerase.

Useful reverse transcriptases include, but are not limited to, HIV-1 reverse transcriptase from human immunodeficiency virus type 1 (PDB 1HMV), HIV-2 reverse transcriptase from human immunodeficiency virus type 2, M-MLV reverse transcriptase from the Moloney murine leukemia virus, AMV reverse transcriptase from the avian myeloblastosis virus, and Telomerase reverse transcriptase that maintains the telomeres of eukaryotic chromosomes.

A polymerase having an intrinsic 3'-5' proofreading exonuclease activity can be useful for some embodiments. Polymerases that substantially lack 3'-5' proofreading exonuclease activity are also useful in some embodiments, for example, in most sequencing embodiments. Absence of exonuclease activity can be a wild type characteristic or a characteristic imparted by a variant or engineered polymerase structure. For example, exo minus Klenow fragment is a mutated version of Klenow fragment that lacks 3'-5' proofreading exonuclease activity. Klenow fragment and its exo minus variant can be useful in a method or composition set forth herein.

A stabilized ternary complex can be attached to a solid support. The solid support can be made from any of a variety of materials set forth herein, for example, above in the definitions or below. Suitable materials may include glass, polymeric materials, silicon, quartz (fused silica), borofloat glass, silica, silica-based materials, carbon, metals, an optical fiber or bundle of optical fibers, sapphire, or plastic materials. The particular material can be selected based on properties desired for a particular use. For example, materials that are transparent to a desired wavelength of radiation are useful for analytical techniques that will utilize radiation of that wavelength. Conversely, it may be desirable to select a material that does not pass radiation of a certain wavelength (e.g. being opaque, absorptive or reflective). Other properties of a material that can be exploited are inertness or reactivity to certain reagents used in a downstream process, such as those set forth herein; or ease of manipulation or low cost of manufacture.

A particularly useful solid support is a particle such as a bead or microsphere as exemplified below. Populations of beads can be used for attachment of populations of stabilized ternary complexes. In some embodiments it may be useful to use a configuration whereby each bead has a single type of stabilized ternary complex (e.g. one allele type per bead). Alternatively, different stabilized ternary complexes need not be separated on a bead-by-bead basis. As such a bead can bear multiple different types of stabilized ternary complexes (e.g. multiple types of alleles per bead). The composition of a bead can vary, depending for example, on the format, chemistry and/or method of attachment to be used. Exemplary bead compositions include solid supports, and chemical functionalities imparted thereto, used in protein and nucleic acid capture methods. Such compositions include, for example, plastics, ceramics, glass, polystyrene, melamine, methylstyrene, acrylic polymers, paramagnetic materials, thoria sol, carbon graphite, titanium dioxide, latex or cross-linked dextrans such as Sepharose™, cellulose, nylon, cross-linked micelles and Teflon', as well as other materials set forth in "Microsphere Detection Guide" from Bangs Laboratories, Fishers Ind., which is incorporated herein by reference.

The geometry of a particle, bead or microsphere also can correspond to a wide variety of different forms and shapes. For example, they can be symmetrically shaped (e.g. spherical or cylindrical) or irregularly shaped (e.g. controlled pore glass). In addition, beads can be, for example, porous, thus increasing the surface area available for capture of ternary complexes or components thereof. Exemplary sizes for beads used herein can range from nanometers to millimeters or from about 10 nm-1 mm.

In particular embodiments, beads can be arrayed or otherwise spatially distinguished. Exemplary bead-based arrays that can be used include, without limitation, those in which beads are associated with a solid support such as those described in U.S. Pat. No. 6,355,431 B1, U.S. Pub. No. 2002/0102578 or PCT Pub. No. WO 00/63437, each of which is incorporated herein by reference. Beads can be located at discrete locations, such as wells, on a solid-phase support, whereby each location accommodates a single bead. Alternatively, discrete locations where beads reside can each include a plurality of beads as described, for example, in U.S. Pub. Nos. 2004/0263923, 2004/0233485, 2004/0132205, or 2004/0125424, each of which is incorporated herein by reference.

Another useful solid support is an array of features. Arrays are particularly useful for multiplex applications wherein a plurality of different ternary complexes are made and used. Compositions and techniques for making and using arrays are set forth in further detail below. Features on an array can be used for attachment of populations of stabilized ternary complexes. In some embodiments, it may be useful to use a configuration whereby each feature has a single type of stabilized ternary complex (e.g. one allele type per feature). Alternatively, different stabilized ternary complexes need not be separated on a feature-by-feature basis. As such, a feature can bear multiple different types of stabilized ternary complexes (e.g. multiple types of alleles per feature).

A stabilized ternary complex or component that is used to make such a complex can be attached to a solid support using any of a variety of methods well known in the art. Such methods include for example, attachment by direct chemical synthesis onto the solid support, chemical attachment, photochemical attachment, thermal attachment, enzymatic attachment and/or absorption. These and other methods are well known in the art and applicable for attachment of proteins, nucleotides or nucleic acids in any of a variety of formats and configurations. Attachment to a solid support can occur via a covalent linkage or via non-covalent interactions. Exemplary non-covalent interactions are those between a ligand-receptor pair such as streptavidin (or analogs thereof) and biotin (or analogs thereof) or between an antibody (or functional fragment thereof such as a Fab or ScFv) and epitope. Other useful receptor-ligand pairs include lectin and carbohydrate, and complementary first and second strands of a nucleic acid.

A polymerase, nucleotide, primer or template that participates in formation of a ternary complex can be attached to a solid support either before or after formation of a stabilized ternary complex. An exemplary embodiment wherein a ternary complex is formed in solution and subsequently attached to a solid support is diagramed in FIG. 2. As exemplified in the Figure, a polymerase can include a ligand moiety (e.g. biotin) that is bound to a solid-phase receptor (e.g. streptavidin) after a stabilized ternary complex is formed. Alternatively, it is possible to bind a ligand moiety of a polymerase to a solid phase receptor (e.g. by binding a biotinylated polymerase to streptavidin beads) prior to formation of the stabilized ternary complex. Thus, a stabilized ternary complex can be formed on a solid support.

Although variability in the order of solid-phase attachment and ternary complex formation is exemplified above for attachment via polymerase, it will be understood that similar variability in the order of steps can occur when other components of the ternary complex have the attachment moiety. Similar variability in the order of steps can occur using linkages other than receptor-ligand interactions. For example, gentle chemistry conditions can be used that allow a chemical attachment moiety to bond covalently with a solid support before or after formation of a ternary complex. Exemplary chemistry conditions and linkages include those used routinely for modifying active proteins and enzymes such as those commercially available from ThermoFisher (Waltham, Mass.), Sigma Aldrich (St. Louis, Mo.) or Promega (Madison Wis.).

Other chemistry conditions and linkages that are useful are those known as "click chemistry" (e.g. U.S. Pat. No. 6,737,236 and U.S. Pat. No. 7,427,678, each incorporated herein by reference in its entirety). Also useful are azide alkyne Huisgen cycloaddition reactions, which use a copper catalyst (e.g. U.S. Pat. No. 7,375,234 and U.S. Pat. No. 7,763,736, each incorporated herein by reference in its entirety). Copper-free Huisgen reactions ("metal-free click") using strained alkynes can be employed. Other useful linkage chemistries include, but are not limited to triazine-hydrazine moieties which can link to aldehyde moieties, for example as described in U.S. Pat. No. 7,259,258, which is incorporated by reference; triazine chloride moieties which can link to amine moieties; carboxylic acid moieties which can link to amine moieties using a coupling reagent, such as EDC, thiol moieties which can link to thiol moieties; alkene moieties which can link to dialkene moieties that are coupled through Diels-Alder reactions; and acetyl bromide moieties which can link thiophosphate moieties, such as those described in PCT Pub. No. WO 2005/065814, which is incorporated by reference. Glass-like surfaces can also be modified with various glass-reactive molecules, such as functionalized silanes, some of which are commercially available through Gelest, Inc.

Accordingly, a method for separating a target allele from a mixture of nucleic acids can include steps of (a) (i) providing a mixture of nucleic acids including a primed template nucleic acid and contacting the mixture with a polymerase and a next correct nucleotide, wherein the template has a target allele, wherein the next correct nucleotide is a cognate nucleotide for the target allele, and (ii) forming a stabilized ternary complex, wherein the stabilized ternary complex includes the polymerase, primed nucleic acid template, and next correct nucleotide, and wherein the stabilized ternary complex is attached to the solid support via a linkage between the polymerase and the solid support or wherein the stabilized ternary complex is attached to the solid support via a linkage between the next correct nucleotide and the solid support; and (b) separating the solid support from the mixture of nucleic acids, thereby separating the target allele from the mixture of nucleic acids.

Optionally, the polymerase or next correct nucleotide is attached to the solid support prior to forming the stabilized ternary complex on the solid support in step (a)(ii). As such, stabilized ternary complex is formed on the solid support. In an alternative option, the polymerase or next correct nucleotide is attached to the solid support after the stabilized ternary complex is formed during or after step (a)(ii). Thus, the ternary complex is formed in solution prior to attaching the ternary complex to the solid support. The latter option is exemplified in FIG. 2.

A method of the present disclosure can include a step of separating a solid support, to which a stabilized ternary complex is attached, from a mixture of nucleic acids. Thus, an allele that was in the mixture, and subsequently attached to the ternary complex, can be separated from the mixture. Separation can be carried out using a method appropriate for the solid support. For example, when a magnetic support is used, for example as shown in FIG. 2, a magnet can be used to attract the support for purposes of separation (e.g. the magnet can be used to remove the support from a vessel containing the mixture or the magnet can be used to retain the solid support in a vessel from which the mixture is removed). Similarly, beads or other particles can be separated from a mixture based on other attractive forces such as the force of gravity (e.g. settling or centrifugation) on materials that are denser than the mixture, electrical attraction of charged materials, optical attraction of dielectric particles, or affinity attraction of the particles to other surfaces (e.g. via receptor-ligand interactions).

Separation of a solid support-bound ternary complex from a fluidic mixture can also be achieved by fluidic flow of the fluid away from the surface of the solid support. For example, a stabilized ternary complex can be attached to a surface of a vessel, such as a flow cell or array surface, and the fluidic mixture can be removed from contact with the surface via gravity (e.g. pouring), pump action (e.g. positive pressure or negative pressure), capillary action, electrophoresis, digital fluidics whereby droplets are moved by electrowetting or other forces (see, for example, US Pub. Nos. 2007/0242105; US 2011/0303542 or 2008/0283414), or the like.

In particular embodiments, a stabilized ternary complex is attached to a flow cell surface or to a solid support in a flow cell. A flow cell allows convenient fluidic manipulation by passing solutions into and out of a fluidic chamber that contacts the support-bound, ternary complex. Exemplary flow cells that can be used are described, for example, in U.S. Pub. Nos. 2010/0111768 A1, WO 05/065814 and US Pub. No. 2012/0270305, each of which is incorporated herein by reference.

Optionally, the provided methods further include a wash step. The wash step can occur before or after any other step in the method. For example, a method set forth herein can optionally include a step of washing a solid support that is attached to a stabilized ternary complex. The wash can provide the advantage of removing contaminants such as components of a mixture from which one or more components of the stabilized ternary complex were derived. In particular embodiments, the wash step occurs under conditions that stabilize the ternary complex. For example, one or more of the stabilizing conditions or stabilizing agents set froth elsewhere herein can be employed during a wash step. Optionally, the wash solution includes nucleotide(s) of the same type as the next correct nucleotide(s) used during formation of the stabilized ternary complex. Including the next correct nucleotide(s) at a sufficient concentration can provide the advantage of stabilizing previously formed ternary complexes from unwanted disassociation. This in turn prevents unwanted loss of target allele due to washing away previously formed ternary complexes. Optionally, the ternary complex has a half-life and the wash step is performed for a duration shorter than the half-life of the ternary complex.

A method of the present disclosure can further include a step of dissociating a target allele from a solid support. For example, dissociation can occur after a solid support-bound, stabilized ternary complex has been removed from a mixture where the complex was formed. Optionally, dissociation can be carried without covalently adding the next correct nucleotide to the 3' end of the primer. This can be achieved by maintaining ternary complex stabilization until the primer is no longer present in the ternary complex. An advantage of releasing unmodified primer is that the primer can be re-used for capturing the same type of allele. For example, the primer can be used in an iterative method to recapture the same allele as set forth in further detail below. The primer can also be used with a new mixture of nucleic acids to capture a new template nucleic acid having the same type of allele.

Exemplary dissociation techniques include, but are not limited to, denaturation of the polymerase, competitive binding of a different nucleic acid to the polymerase to cause release of the target allele, incubation of the ternary complex in a solution that is devoid of next correct nucleotide, in a solution that is devoid of primed template, or in a solution having a concentration of next correct nucleotide or primed template that is substantially below the dissociation constant ($K_d$) of the polymerase for the next correct nucleotide or primed template, respectively. In some embodiments, the ternary complex can be incubated with a nucleotide that is different from the next correct nucleotide (e.g. a cognate nucleotide for a different allele than the target allele). This dissociation method provides an advantage of being relatively gentle and specific such that dissociation of the desired allele is selected over other alleles that may be present as contaminants.

Alternatively, a step of dissociating a target allele from a solid support can be carried out by extending the primer to incorporate a next correct nucleotide. The nucleotide that is incorporated can be a nucleotide molecule that was present in the stabilized ternary complex when it was formed in a mixture and/or when the complex was separated from the mixture. Alternatively, a different nucleotide molecule can enter the ternary complex and then be incorporated into the primer. Thus, the incorporation step can involve replacing a nucleotide from a prior step and incorporating another nucleotide into the 3'-end of the primer. The incorporation step can involve releasing a nucleotide from within a ternary complex and incorporating a nucleotide of a different kind into the 3'-end of the primer.

Optionally, the nucleotide that is incorporated can have an exogenous label. An advantage of using a label is the ability to confirm the identity of the next correct nucleotide by detecting the label on the primer. Alternatively, the nucleotide that is incorporated will lack an exogenous label that is detected.

Accordingly, the methods described herein optionally include an incorporation step. The incorporation step involves covalently incorporating one or more nucleotides at the 3'-end of a primer hybridized to a template nucleic acid. In some embodiments, only a single nucleotide is incorporated at the 3'-end of the primer. For example, the 3' position of the nucleotide can be modified to include a 3' terminator moiety. The 3' terminator moiety may be a reversible terminator or may be an irreversible terminator. Optionally, the reversible terminator nucleotide includes a 3'-ONH$_2$ moiety attached at the 3' position of the sugar moiety. Further examples of useful reversible terminator moieties are described, for example, in Bentley et al., Nature 456:53-59 (2008), WO 04/018497; U.S. Pat. No. 7,057,026; WO 91/06678; WO 07/123744; U.S. Pat. No. 7,329,492; U.S. Pat. No. 7,211,414; U.S. Pat. No. 7,315,019; U.S. Pat. No. 7,405,281, and US 2008/0108082, each of which is incorporated herein by reference. Optionally, multiple nucleotides are incorporated at the 3'-end of the primer. For example, the nucleotide that is incorporated can include a 3'-hydroxyl group that is capable of being further extended after incorporation. In some embodiments, the incorporation step is part of a sequencing technique, amplification technique, or other technique carried out using ternary complex that has been captured using a method set forth herein.

Incorporated nucleotides alternatively can be unlabeled nucleotides, or detectably labeled nucleotide analogs. Whether labeled or not, the nucleotides can be terminator nucleotides that are permanently or reversibly prevented from being extended once incorporated into a primer. The polymerase can dissociate from primed template after nucleotide incorporation. Exemplary reagents and conditions for incorporating nucleotides into the primed template of a ternary complex are set forth in commonly owned U.S. patent application Ser. No. 14/805,381, now published as US Pub. No. 2017/0022553, and 62/375,379, which is incorporated by reference in U.S. Ser. No. 15/677,870, each of which is incorporated herein by reference.

A target allele or other target sequence can be captured using an iterative method whereby steps of a method set forth herein are repeated. The methods set forth herein are well suited to iteration because the nucleic acid primer need not be consumed or modified following use to capture a target sequence. This contrasts with other methods of nucleic acid capture where a primer is extended to incorporate an affinity labeled nucleotide. Once the primer has been modified in this way it has been spent and must be replaced or chemically reverted for use in a repetition of the primer extension step.

An advantage of the iterative approach provided by the current disclosure is that each iteration can further purify the target sequence allowing the nucleic acid to be isolated from other biological materials including other nucleic acids having similar sequences (e.g. other alleles at the same locus as the target allele). The reagents can be re-used thereby providing a cost- and time-effective alternative to other methods that consume primers and other reagents.

Accordingly, the present disclosure provides a method for separating a target allele from a mixture of nucleic acids. The method can include steps of (a) providing a mixture of nucleic acids in fluidic contact with a stabilized ternary complex that is attached to a solid support, wherein the stabilized ternary complex includes a polymerase, primed nucleic acid template, and next correct nucleotide, wherein the template has a target allele, wherein the next correct nucleotide is a cognate nucleotide for the target allele, and wherein the stabilized ternary complex is attached to the solid support via a linkage between the polymerase and the solid support or via a linkage between the nucleotide and the solid support; (b) separating the solid support from the mixture of nucleic acids, thereby separating the target allele from the mixture of nucleic acids; (c) dissociating the template having the target allele from the separated solid support; (d) forming a solution including a second stabilized ternary complex that includes the formerly dissociated template, a polymerase, and a next correct nucleotide that is a cognate nucleotide for the target allele, wherein the polymerase or the next correct nucleotide is attached to a solid support; and (e) separating the solid support of step (d) from the solution, thereby separating the formerly dissociated template having the target allele from the solution. The method can further include an optional step: (f) dissociating the formerly dissociated template from the solid support separated in step (e).

Also provided is a method for separating a first allele of a locus from a second allele at the locus. The method can include steps of (a) providing a mixture including the second allele in fluidic contact with a stabilized ternary complex that is attached to a solid support, wherein the stabilized ternary complex includes a polymerase, primer hybridized to a nucleic acid template, and next correct nucleotide, wherein the template has the first allele, wherein the next correct nucleotide is a cognate nucleotide for the first allele or the 3' end of the primer has a cognate nucleotide for the first allele, and wherein the stabilized ternary complex is attached to the solid support via a linkage between the polymerase and the solid support or via a linkage between the next correct nucleotide and the solid support; (b) separating the solid support from the mixture of nucleic acids, thereby separating the first allele from the second allele; (c) dissociating the template having the first allele from the separated solid support; (d) forming a solution including a second stabilized ternary complex that includes the formerly dissociated template, a polymerase, and a next correct nucleotide, wherein the polymerase or the next correct nucleotide is attached to a solid support; and (e) separating the solid support of step (d) from the solution, thereby separating the formerly dissociated template having the first allele from the solution. The method can further include an optional step: (f) dissociating the formerly dissociated template from the solid support separated in step (e).

In particular embodiments of the above iterative methods, the same solid support is used for step (d) as was used in step (a). This can provide cost savings compared to using a new solid support in step (d). Nevertheless, in some embodiments different solid supports are used in steps (d) and (a). The solid supports used in each step can be of the same type or different type. Any of a variety of solid supports set forth herein or otherwise known in the art can be used.

Similarly, the same polymerase can optionally be used for step (d) as was used in step (a). Again, this can provide cost savings compared to using a new polymerase in step (d). Nevertheless, in some embodiments different polymerases are used in steps (d) and (a). The polymerases used in each step can be of the same type or different type. Any of a variety of polymerases set forth herein or otherwise known in the art can be used.

Typically, the same primer is used for step (a) and step (d). However, in some embodiments, a new primer can be used in step (d). The new primer will typically be of the same type as the previously used primer (i.e. the two primers can have the same sequence and be of the same length). However, if desired primers of different length or sequence can be used.

A method of the present disclosure can be carried out in a multiplex format whereby multiple different types of nucleic acids are processed in parallel during one or more steps set forth herein. Although it is also possible to serially process different types of nucleic acids using one or more steps of the methods set forth herein, parallel processing can provide cost savings, time savings and uniformity of conditions.

Accordingly, this disclosure provides a method for separating a plurality of target alleles from a mixture of nucleic acids. The method can include steps of (a) providing a mixture of nucleic acids in fluidic contact with a plurality of stabilized ternary complexes that are solid support-attached, wherein the stabilized ternary complexes each includes a polymerase, primed nucleic acid template, and next correct nucleotide, wherein the template has a target allele, wherein the next correct nucleotide is a cognate nucleotide for the target allele, and wherein each of the stabilized ternary complexes is attached to the solid support via a linkage between the polymerase and the solid support or via a linkage between the next correct nucleotide and the solid support; and (b) separating the solid support from the mixture of nucleic acids, thereby separating the target alleles from the mixture of nucleic acids.

The disclosure further provides a method for separating first alleles at a plurality of loci from second alleles at the plurality of loci, respectively. The method can include steps of (a) providing a mixture of the second alleles at the plurality of loci, respectively, in fluidic contact with a plurality of stabilized ternary complexes that are solid support-attached, wherein the stabilized ternary complexes each include a polymerase, primed nucleic acid template, and next correct nucleotide, wherein the template includes a first allele, wherein the next correct nucleotide is a cognate nucleotide for the first allele or the 3' end of the primer includes a cognate nucleotide for the first allele, and wherein each of the stabilized ternary complexes is attached to the solid support via a linkage between the polymerase and the solid support or via a linkage between the next correct nucleotide and the solid support; and (b) separating the solid support from the mixture of nucleic acids, thereby separating the first alleles from the second alleles at the plurality of loci.

A particularly useful solid support for use in multiplex embodiments is one having an array of features. For example, each stabilized ternary complex can be attached to an array via a linkage to a particular feature of the array, thereby separating templates comprising different alleles from each other. Any of a variety of arrays known in the art can be modified for use in a method or composition set forth herein. For example, linkages made from commercial arrays (or other nucleic acid arrays) to nucleic acid probes can be replaced with linkages set forth herein for attaching polymerases or nucleotides to surfaces. In other embodiments, polymerases or nucleotides can be attached to oligonucleotide moieties that are complementary to probes located on nucleic acid arrays. In such embodiments, the nucleotide or polymerase can be attached to the surface via hybridization or crosslinking of the complementary strands. If desired a template and/or primer can be attached to a feature of an array.

Exemplary array substrates that can be useful include, without limitation, a BeadChip™ Array available from Illumina, Inc. (San Diego, Calif.) or arrays such as those described in U.S. Pat. Nos. 6,266,459; 6,355,431; 6,770, 441; 6,859,570; or U.S. Pat. No. 7,622,294; or PCT Publication No. WO 00/63437, each of which is incorporated herein by reference. Further examples of commercially available array substrates that can be used include, for example, an Affymetrix GeneChip' array. A spotted array substrate can also be used according to some embodiments. An exemplary spotted array is a CodeLink™ Array available from Amersham Biosciences. Another array that is useful is one that is manufactured using inkjet printing methods such as SurePrint™ Technology available from Agilent Technologies.

Other useful array substrates include those that are used in nucleic acid sequencing applications. For example, arrays that are used to attach amplicons of genomic fragments (often referred to as clusters) can be particularly useful. Examples of substrates that can be modified for use herein include those described in Bentley et al., Nature 456:53-59 (2008), PCT Pub. Nos. WO 91/06678; WO 04/018497 or WO 07/123744; U.S. Pat. Nos. 7,057,026; 7,211,414; 7,315, 019; 7,329,492 or U.S. Pat. No. 7,405,281; or U.S. Pat. App. Pub. No. 2008/0108082, each of which is incorporated herein by reference.

A multiplex embodiment can be carried out using allele-specific nucleotides and locus primers of the type exemplified in FIG. 1A. More specifically, the next correct nucleotide that is present in a stabilized ternary complex can be a cognate nucleotide for a first allele at a locus such that the next correct nucleotide is not a cognate nucleotide for a second allele at the locus. Loci having alleles that span a variety of different nucleotide types can be treated sequentially. For example, the plurality of loci present in a multiplex format can span four different types of nucleotides. In this example, a first iteration of the multiplex method can be carried out to form a plurality of stabilized ternary complexes having cognate nucleotides for only a first type of the four different types of nucleotides. Then a second iteration of the multiplex method can be carried out to form a plurality of stabilized ternary complexes having cognate nucleotides for only a second type of the four different types of nucleotides, the second type being different from the first type. In a third iteration, a plurality of stabilized ternary complexes can be formed having cognate nucleotides for only a third type of the four different types of nucleotides, the third type being different from the first and second types. In a fourth iteration, a plurality of stabilized ternary complexes can be formed having cognate nucleotides for only a fourth type of the four different types of nucleotides, the fourth type being different from the first, second and third types.

In some multiplex embodiments, allele-specific primers of the type exemplified in FIG. 1A can be used. More specifically, the 3' end of each primer can have a cognate nucleotide for a first allele at a locus such that the 3' end of the primer does not have a cognate nucleotide for a second allele at the locus. An advantage of using an allele-specific primer in a multiplex format is that loci having alleles that span a variety of different nucleotide types can be treated in parallel. Because alleles are distinguished by the presence or absence of cognate nucleotides at the 3' ends of the primers and not by the next correct nucleotide, a mixture of ternary complexes with different loci and alleles can be in simultaneous contact with more than one type of next correct nucleotides. Of course, if desired, a mixture can include a plurality ternary complexes that have been formed with allele-specific primers and only a subset of the next correct nucleotide types that could have formed stabilized ternary complexes in the mixture. The subset can include cognate nucleotides for no more than 1, 2, 3 or 4 different types of nucleotides in the plurality of loci that are present.

One or more template nucleic acids that are captured using a method of the present disclosure can be used in a variety of subsequent applications. For example, the template nucleic acid(s) can be used in a preparative method such as cloning of a gene or gene fragment. The template can be amplified using a method such as polymerase chain reaction (PCR), rolling circle amplification (RCA), multiple displacement amplification (MDA) or the like. In some cases, the primer that was used to form the ternary complex in a capture method can also be used for amplification. Generally, a template that is captured using a method set forth herein can be manipulated using methods known in the art including, but not limited to, those described in Sambrook et al., *Molecular Cloning: A Laboratory Manual*, 3rd edition, Cold Spring Harbor Laboratory, New York (2001) or in Ausubel et al., *Current Protocols in Molecular Biology*, John Wiley and Sons, Baltimore, Md. (1998), each of which is incorporated herein by reference.

In particular embodiments, one or more template nucleic acid(s) that are captured using a method set forth herein can be used in an analytical method, for example, real time polymerase chain reaction (rtPCR), quantitative PCR (qPCR), nucleic acid sequencing, genotyping analysis, expression analysis or the like. Several of these methods employ a step of extending a primer along a template to be analyzed. In some cases, the primer that was used to form the ternary complex in a capture method can also be used for primer extension in an analytical technique.

Optionally, sequencing is carried out as described in commonly owned U.S. Ser. No. 14/805,381, now published as U.S. Pub. No. 2017/0022553 A1, which is incorporated herein by reference. Briefly, methods for determining the sequence of a template nucleic acid molecule can be based on formation of a ternary complex (between polymerase, primed nucleic acid and cognate nucleotide) under specified conditions. The method can generally include an examination step prior to incorporation of a nucleotide. The examination step can involve providing a template nucleic acid molecule primed with a primer; contacting the primed template nucleic acid molecule with a first reaction mixture that includes a polymerase and at least one nucleotide molecule; monitoring the interaction of the polymerase with the primed template nucleic acid molecule in the presence of the nucleotide molecule, without chemical incorporation of the nucleotide molecule into the primed template nucleic acid; and identifying a next base in the template nucleic acid using the monitored interaction of the polymerase with the primed template nucleic acid molecule in the presence of the nucleotide molecule. In this procedure, ternary complex stabilization and binary complex destabilization advantageously enhance discrimination between correct and incorrect nucleotides.

Sequencing-by-synthesis (SBS) techniques can also be used. SBS generally involves the enzymatic extension of a nascent primer through the iterative addition of nucleotides against a template strand to which the primer is hybridized. SBS can utilize nucleotide monomers that have a terminator moiety or those that lack any terminator moieties. Methods utilizing monomers having terminators include, for example, those described in WO 04/018497, U.S. Pat. No. 7,057,026, WO 91/106678, WO 07/123744, U.S. US 2007/0166705, US 2006/0188901, US 2006/0240439, US 2006/0281109, WO 05/065814, US 2005/0100900, WO 06/064199 or WO 07010251, the disclosures of which are incorporated herein by reference. Also useful are SBS methods that are commercially available from Illumina, Inc., San Diego Calif.

Some SBS embodiments include detection of a proton released upon incorporation of a nucleotide into an extension product. For example, sequencing based on detection of released protons can use an electrical detector and associated techniques that are commercially available from Thermo Fisher (Waltham, Mass.) or sequencing methods and systems described in US Pat. App. Pub. Nos. 2009/0026082 A1; 2009/0127589 A1; 2010/0137143 A1; or 2010/0282617 A1, each of which is incorporated herein by reference.

Other sequencing procedures can be used, such as pyrosequencing. Pyrosequencing detects the release of inorganic pyrophosphate (PPi) as particular nucleotides are incorporated into a nascent primer hybridized to a template nucleic acid strand (Ronaghi, et al., *Analytical Biochemistry* 242 (1), 84-9 (1996); Ronaghi, *Genome Res.* 11 (1), 3-11 (2001); Ronaghi et al. *Science* 281 (5375), 363 (1998); U.S. Pat. Nos. 6,210,891; 6,258,568 and 6,274,320, each of which is incorporated herein by reference). In pyrosequencing, released PPi can be detected by being converted to adenosine triphosphate (ATP) by ATP sulfurylase, and the resulting ATP can be detected via luciferase-produced photons. Thus, the sequencing reaction can be monitored via a luminescence detection system.

Sequencing-by-ligation reactions are also useful including, for example, those described in Shendure et al. *Science* 309:1728-1732 (2005); U.S. Pat. No. 5,599,675; and U.S. Pat. No. 5,750,341, each of which is incorporated herein by reference. Some embodiments can include sequencing-by-hybridization procedures as described, for example, in Bains et al., *Journal of Theoretical Biology* 135 (3), 303-7 (1988); Drmanac et al., *Nature Biotechnology* 16, 54-58 (1998); Fodor et al., *Science* 251 (4995), 767-773 (1995); and WO 1989/10977, each of which is incorporated herein by reference. In both sequencing-by-ligation and sequencing-by-hybridization procedures, primers that are hybridized to nucleic acid templates are subjected to repeated cycles of extension by oligonucleotide ligation. Typically, the oligonucleotides are fluorescently labeled and can be detected to determine the sequence of the template.

Some embodiments can utilize methods involving the real-time monitoring of DNA polymerase activity. For example, nucleotide incorporations can be detected through fluorescence resonance energy transfer (FRET) interactions between a fluorophore-bearing polymerase and gamma-phosphate-labeled nucleotides, or with zeromode waveguides (ZMW). Techniques and reagents for sequencing via FRET and or ZMW detection are described, for example, in Levene et al. *Science* 299, 682-686 (2003); Lundquist et al. *Opt. Lett.* 33, 1026-1028 (2008); Korlach et al. *Proc. Natl. Acad. Sci. USA* 105, 1176-1181 (2008), the disclosures of which are incorporated herein by reference.

In some embodiments, sequencing methods utilize a polymerase that is attached to a ZMW or other solid-support feature. A ternary complex that is captured in a method set forth herein, or a component thereof, can be attached to a ZMW or other solid support used in sequencing techniques set forth above or otherwise known in the art.

Another useful application for a template nucleic acid captured by a method of the present disclosure is gene expression analysis. Gene expression can be detected or quantified using RNA sequencing techniques, such as those, referred to as digital RNA sequencing. RNA sequencing techniques can be carried out using sequencing methodologies known in the art such as those set forth above. Gene expression can also be detected or quantified using hybridization techniques carried out by direct hybridization to an array or using a multiplex assay, the products of which are detected on an array. An array of the present disclosure can also be used to determine genotypes for a genomic DNA sample from one or more individual. Exemplary methods for array-based expression and genotyping analysis that can be carried out using a template nucleic acid captured by methods of the present disclosure are described in U.S. Pat. Nos.

7,582,420; 6,890,741; 6,913,884 or U.S. Pat. No. 6,355,431 or US Pub. Nos. 2005/0053980; 2009/0186349 or 2005/0181440, each of which is incorporated herein by reference.

Furthermore, nucleic acids that are separated using a method set forth herein can be detected in a method set forth in U.S. Provisional Application No. 62/448,630, filed Jan. 20, 2017, US Pat. App. Docket No. OMNI-014 (097128-1036629 (022PV1), having the title "GENOTYPING BY POLYMERASE BINDING," filed concurrently with the present application, and incorporated herein by reference in its entirety. More specifically, one or more alleles that are separated using a method set forth herein can be detected in a polymerase-based method for detecting or identifying target alleles of interest. Embodiments of the methods exploit the specificity with which a polymerase can form a stabilized ternary complex with a primed template and a next correct nucleotide. For example, a stabilized ternary complex can be formed between a polymerase, primed template having a target allele and cognate nucleotide for the allele. An advantage of the methods is that polymerase specificity allows a target allele to be distinguished from other nucleic acids, including for example, other alleles that differ from the target allele, in some cases by only a single nucleotide. For example, a ternary complex can be formed between a polymerase, a primed template encoding a target single nucleotide polymorphism (SNP) allele and a cognate nucleotide for the SNP allele. Detection of the ternary complex will result in selective detection of the SNP allele, compared to a non-target SNP allele at the same locus, because the cognate nucleotide is selective for the target SNP when forming a ternary complex with the polymerase.

Methods and compositions set forth herein can be used to detect rare alleles (e.g. DNA- or RNA-based) containing various mutations within their sequences. The methods are well suited to detect even rare variant alleles from pools of purified or semi-purified oligonucleotides containing wild-type DNA sequences of the same locus, as well as other unrelated sequences. Useful primer-nucleotide combinations that can be used to form allele-specific ternary complexes in a detection method include those shown in FIG. 1A and FIG. 1B.

In an exemplary embodiment, a first allele-specific primer can be present at a first feature of an array and a second allele-specific primer can be present at a second feature of the array. The array can be contacted with template nucleic acids, polymerases and a mixture of four different nucleotide types all having the same label. A mismatch between the primer and nucleic acid template will inhibit polymerase binding, whereas a matched primer template can bind polymerase and a next correct nucleotide to form a stabilized ternary complex. Optionally the array can be washed. The array can then be detected using a device that spatially resolves the features and senses the presence or absence of the labels.

An alternative array format for detection of alleles can utilize locus-specific primers and allele-specific cognate nucleotides that are distinguishably labelled. In the first step, nucleic acid templates having different alleles can be hybridized to a feature on an array having multiple copies of the locus-specific primer. As such, two different alleles can bind at the feature. Polymerases can then be bound to the primer-template hybrids in the presence of two different nucleotide types having distinct labels to form stabilized ternary complexes. Optionally the array can be washed. The array can then be detected using a device that distinguishes the two labels.

Accordingly, one or more allele(s) separated in a method set forth herein can be detected in a method that follows.

A method for identifying target alleles can include steps of (a) forming a plurality of stabilized ternary complexes at a plurality of features on an array, wherein the stabilized ternary complexes each has a polymerase, a template nucleic acid having a target allele of a locus, a primer hybridized to the locus, and a next correct nucleotide having a cognate in the locus, wherein either (i) the primer is an allele-specific primer having a 3' nucleotide that is a cognate nucleotide for the target allele, or (ii) the primer is a locus-specific primer and the next correct nucleotide hybridizes to the target allele; and (b) detecting stabilized ternary complexes at the features, thereby identifying the target alleles.

In some embodiments, the method for identifying target alleles can include steps of (a) providing an array of features, wherein different locus-specific primers are attached at different features of the array; (b) contacting the array with a plurality of nucleic acid templates, polymerases and nucleotides to form a plurality of stabilized ternary complexes at a plurality of the features, wherein the stabilized ternary complexes each has a polymerase, template nucleic acid having a target allele of a locus, a locus-specific primer hybridized to the locus, and a next correct nucleotide that is a cognate to the target allele; and (c) detecting stabilized ternary complexes at the features, thereby identifying the target alleles.

An alternative embodiment of the method for identifying target alleles can include steps of (a) providing an array of features, wherein different allele-specific primers are attached at different features of the array; (b) contacting the array with a plurality of nucleic acid templates, polymerases and nucleotides to form a plurality of stabilized ternary complexes at a plurality of the features, wherein the stabilized ternary complexes each has a polymerase, template nucleic acid having a target allele of a locus, an allele-specific primer hybridized to the locus, and a next correct nucleotide having a cognate in the locus, wherein the 3' end of the allele-specific primer has a cognate nucleotide for the target allele; and (c) detecting stabilized ternary complexes at the features, thereby identifying the target alleles.

A method for identifying target alleles in a mixture of nucleic acids can include steps of (a) providing an array of features, wherein different locus-specific primers are attached at a first subset of the features of the array, and wherein different allele-specific primers are attached at a second subset of the features of the array; (b) contacting the array with a plurality of nucleic acid templates, polymerases and nucleotides to form a plurality of stabilized ternary complexes at a plurality of the features, wherein the stabilized ternary complexes at the first subset of features each has a polymerase, template nucleic acid having a target allele of a locus, a locus-specific primer hybridized to the locus, and a next correct nucleotide that is a cognate to the target allele, wherein the stabilized ternary complexes at the second subset of features each has a polymerase, template nucleic acid having a target allele of a locus, an allele-specific primer hybridized to the locus, and a next correct nucleotide having a cognate in the locus, and wherein the 3' end of the allele-specific primer has a cognate nucleotide for the target allele; and (c) detecting stabilized ternary complexes at the features, thereby identifying the target alleles.

Also provided is a method for identifying target alleles in a mixture of nucleic acids, that includes steps of (a) providing an array of features, wherein different template nucleic acids are attached at different features of the array; (b) contacting the array with a plurality of primers, polymerases and nucleotides to form a plurality of stabilized ternary complexes at a plurality of the features, wherein the stabilized ternary complexes at the features each has a polymerase, a template nucleic acid attached to a feature of the array and having a target allele of a locus, a primer hybridized to the locus, and a next correct nucleotide having a cognate in the locus, wherein either (i) the primer is an allele-specific primer having a 3' nucleotide that is a cognate nucleotide for the target allele, or (ii) the primer is a locus-specific primer and the next correct nucleotide hybridizes to the target allele; and (c) detecting stabilized ternary complexes at the features, thereby identifying the target alleles.

Further provided is a method for identifying target alleles in a mixture of nucleic acids that includes steps of (a) providing an array of features, wherein polymerases are attached at features of the array; (b) contacting the array with a plurality of primers, template nucleic acids and nucleotides to form a plurality of stabilized ternary complexes at a plurality of the features, wherein the stabilized ternary complexes at the features each has a polymerase that is attached at a feature of the array, template nucleic acid having a target allele of a locus, a primer hybridized to the locus, and a next correct nucleotide having a cognate in the locus, wherein either (i) the primer is an allele-specific primer having a 3' nucleotide that is a cognate nucleotide for the target allele, or (ii) the primer is a locus-specific primer and the next correct nucleotide hybridizes to the target allele; and (c) detecting stabilized ternary complexes at the features, thereby identifying the target alleles.

Example 1

Distinguishing the Next Correct Nucleotide From a Mismatched Nucleotide.

Methods & Materials. Polymerase buffer: 20 mM Tris, pH 8, 300 mM NaCl, 5 mM DTT, 100 µM dNTP, 150 nM Kienow, 0.01% BSA, 0.02% Tween-20, 10 mM $MgCl_2$. Exam buffer: 20 mM Tris, pH 8, 300 mM NaCl, 5 mM DTT, 100 µM dNTP, 150 nM Klenow, 0.01% BSA, 0.02% Tween-20. Incorporation buffer: 20 mM Tris, pH 8, 300 mM NaCl, 5 mM DTT, 0.01% BSA, 0.02% Tween-20, 10 mM $MgCl_2$. Wash Buffer: 20 mM Tris, pH 8, 300 mM NaCl, 5 mM DTT, 0.01% BSA, 0.02% Tween-20.

Figure 4:
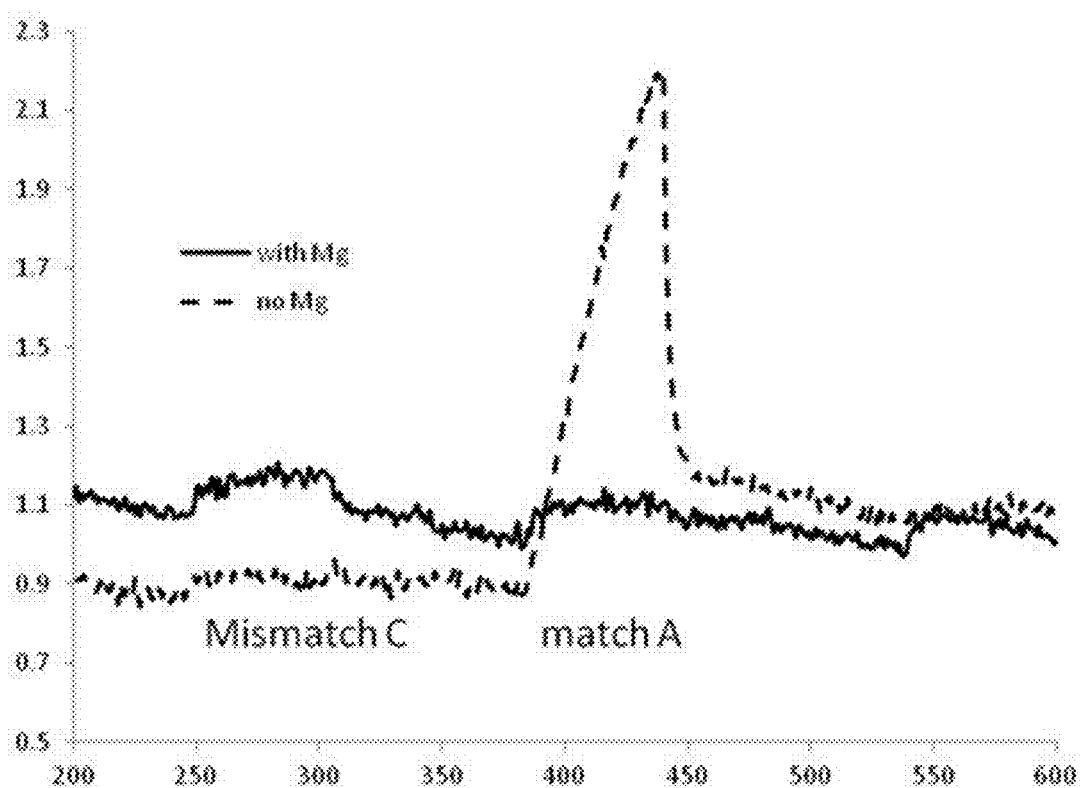
FIG. 4 is a graph showing the results of a binding assay using non-labeled optical detection methods where primed template, polymerase and nucleotide was incubated together in the presence or absence of magnesium.

FIG. 4 shows the results of a binding assay using polymerase, primed template, and nucleotide (either matched or mismatched with the next base in the template), where magnesium was present or absent during the binding assay. The first delivered nucleotide was dCTP (C:T mismatch) and the second delivery was dATP (A:T match). The solid line in FIG. 3 shows the results with Polymerase buffer. The pre-steady state rate constants were 0.0106 and 0.0084 for the match A and mismatch C steps, respectively. The difference was too small to accurately discriminate the cognate base. The dashed line in FIG. 4 represents a magnesium free binding step in Exam buffer, followed by soaking in incorporation buffer. A signal threshold of 1.1 nm allowed accurate identification of the correct base. These results show that the sensing platform was unable to discriminate a match from mismatch base when magnesium was included in the buffer during examination (Polymerase Buffer, solid line, FIG. 4). In contrast, binding in the absence of magnesium provided very large discrimination between correct and incorrect base (Exam Buffer, dashed line, FIG. 4). The correct base sequence was determined by signal thresholding rather than binding rates.

Example 2

Effect of Salt Concentration on Match/Mismatch Base Discrimination

The FORTEBIO® Octet instrument (Red384 or qk) (Menlo Park, Calif.) uses biolayer interferometry to measure binding reactions at the surface of a fiber optic tip. In this example, the tips were functionalized with streptavidin (SA) to enable binding to 5' biotin labeled DNA templates hybridized with a primer that is complementary to sequences near the 3' end of the template.

Experimental Conditions:

PhiX_matchC and phiX_matchA were loaded onto individual tips. Primer-template was loaded onto the tips at between 100 and 500 nM in 1-2×PBS containing 0.01-0.02% BSA and 0.01-0.02% Tween 20 (loading buffer). The FP2 primer was in 1.25-2 fold excess over template. Loading was monitored by change in signal and usually reached a plateau within 5 minutes at 30 degrees C. Tips were soaked in Loading buffer for 1-5 minutes to remove unbound DNA material. For base calling, the tips were soaked in solutions containing IX Taq buffer (10 mM Tris-HCl, 50 mM KCl, pH 8.3, 25° C., magnesium free) supplemented with 0.01-0.02% BSA and 0.01-0.02% Tween 20 (LS buffer), 100 nM polymerase enzyme, 100 µM NTP, and varying concentrations of additional NaCl from 50 to 300 mM. The phiX_matchC duplex will form a ternary complex and show an increase in binding signal because the next correct nucleotide (cognate) is presented. The phiX_matchA should not because it is an incorrect nucleotide (noncognate).

Figure 5:
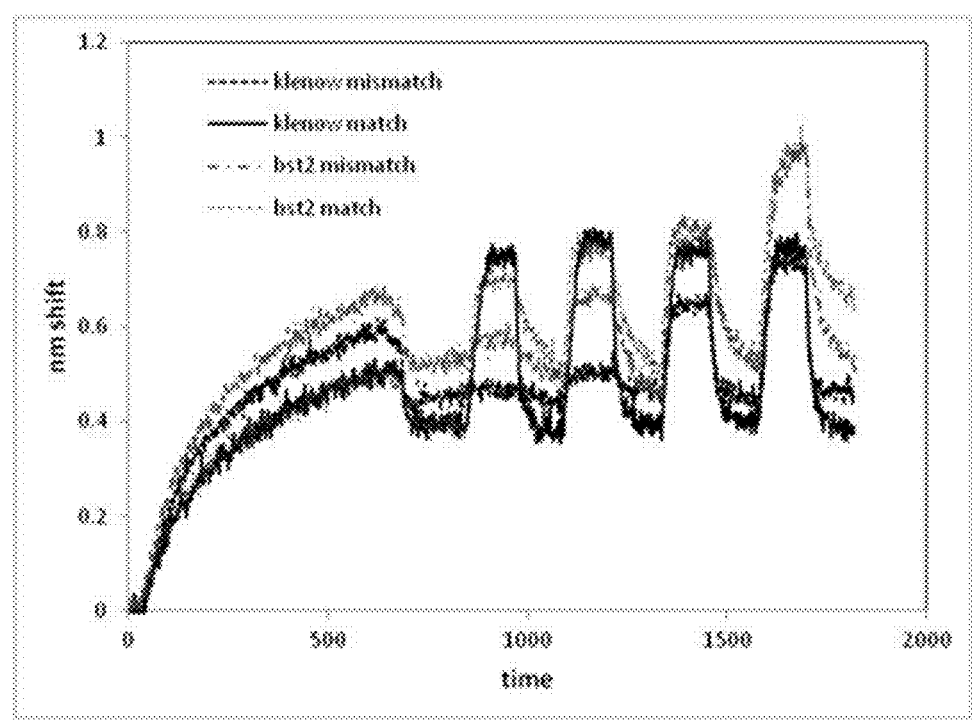
FIG. 5 is a graph showing the effects of salt concentration on match and mismatch base discrimination effects using biolayer interferometry on a FORTEBIO® Octet instrument (Menlo Park, Calif.).

Results:

At standard reaction conditions both templates bound polymerase enzyme. However, as the salt concentration increased the binding affinity of the noncognate complex decreased while binding affinity of the cognate complex remained high. Thus, the signal to noise ratio (SNR) of base discrimination increased such that the next correct base was easily identified during this examination step (FIG. 5). Sodium chloride (NaCl) was used in this example but salts such as KCl, $NH_2(SO_4)$, potassium glutamate, and others known in the art can be used. Polymerases that show differences in binding affinity between correct and incorrect nucleotides included Klenow, Bst2.0, Bsu, and Taq.

Throughout this application various publications, patents and/or patent applications have been referenced. The disclosures of these documents in their entireties are hereby incorporated by reference in this application.

A number of embodiments have been described. Nevertheless, it will be understood that various modifications may be made. Accordingly, other embodiments are within the scope of the following claims.

What is claimed is:

1. A method for separating a target allele from a mixture of nucleic acids, comprising
   (a) providing a mixture of nucleic acids in fluidic contact with a stabilized ternary complex that is attached to a solid support,
      wherein the stabilized ternary complex comprises a polymerase, primed nucleic acid template, and next correct nucleotide,
      wherein the template comprises a target allele,
      wherein the next correct nucleotide is a cognate nucleotide for the target allele, and
      wherein the stabilized ternary complex is attached to the solid support via a linkage between the polymerase and the solid support or via a linkage between the next correct nucleotide and the solid support; and (b) separating the solid support from the mixture of nucleic acids, thereby separating the target allele from the mixture of nucleic acids.

2. The method of claim 1, wherein the target allele occurs at a locus and the mixture of nucleic acids further comprises another allele at the locus.

3. The method of claim 2, wherein the separating of the solid support from the mixture of nucleic acids thereby separates the target allele from the other allele at the locus.

4. The method of claim 2, wherein the target allele is a minor allele at the locus, and wherein the minor allele frequency is less than 5% at the locus.

5. The method of claim 1, further comprising
(c) dissociating the template comprising the target allele from the separated solid support.

6. The method of claim 1, wherein step (b) further comprises washing the separated solid support to further remove components of the mixture.

7. The method of claim 6, further comprising
(d) forming a solution comprising second stabilized ternary complex that comprises the formerly dissociated template, a polymerase, and a next correct nucleotide that is a cognate nucleotide for the target allele, wherein the polymerase or the next correct nucleotide is attached to a solid support.

8. The method of claim 7, further comprising
(e) separating the solid support of step (d) from the solution, thereby separating the formerly dissociated template comprising the target allele from the solution.

9. The method of claim 8, further comprising
(f) dissociating the formerly dissociated template from the solid support separated in step (e).

10. The method of claim 7, wherein the solid support of step (a) is the same as the solid support of step (d).

11. The method of claim 7, wherein the polymerase of step (a) is the same as the polymerase of step (d).

12. The method of claim 1, wherein step (a) further comprises providing a mixture of nucleic acids comprising the template and contacting the mixture with the polymerase and the next correct nucleotide, thereby providing the mixture of nucleic acids and the stabilized ternary complex.

13. The method of claim 12, wherein the polymerase or the next correct nucleotide is attached to the solid support prior to forming the stabilized ternary complex on the solid support.

14. The method of claim 12, wherein the stabilized ternary complex is formed in solution prior to attaching the ternary complex to the solid support.

15. The method of claim 1, wherein the linkage comprises a receptor-ligand association.

16. The method of claim 1, wherein the ternary complex lacks exogenous labels.

17. The method of claim 1, wherein the next correct nucleotide lacks exogenous labels.

18. A method for separating a plurality of target alleles from a mixture of nucleic acids, comprising
(a) providing a mixture of nucleic acids in fluidic contact with a plurality of stabilized ternary complexes that are solid support-attached,
wherein the stabilized ternary complexes each comprises a polymerase, primed nucleic acid template, and next correct nucleotide,
wherein the template comprises a target allele,
wherein the next correct nucleotide is a cognate nucleotide for the target allele, and
wherein each of the stabilized ternary complexes is attached to the solid support via a linkage between the polymerase and the solid support or via a linkage between the next correct nucleotide and the solid support; and
(b) separating the solid support from the mixture of nucleic acids, thereby separating the target alleles from the mixture of nucleic acids.

19. A method for separating a first allele of a locus from a second allele at the locus, comprising
(a) providing a mixture comprising the second allele in fluidic contact with a stabilized ternary complex that is attached to a solid support,
wherein the stabilized ternary complex comprises a polymerase, primer hybridized to a nucleic acid template, and next correct nucleotide,
wherein the template comprises the first allele,
wherein the next correct nucleotide is a cognate nucleotide for the first allele or the 3' end of the primer comprises a cognate nucleotide for the first allele, and
wherein the stabilized ternary complex is attached to the solid support via a linkage between the polymerase and the solid support or via a linkage between the next correct nucleotide and the solid support; and
(b) separating the solid support from the mixture of nucleic acids, thereby separating the first allele from the second allele.

20. A method for separating first alleles at a plurality of loci from second alleles at the plurality of loci, respectively, comprising
(a) providing a mixture of the second alleles at the plurality of loci, respectively, in fluidic contact with a plurality of stabilized ternary complexes that are solid support-attached,
wherein the stabilized ternary complexes each comprises a polymerase, primed nucleic acid template, and next correct nucleotide,
wherein the template comprises a first allele,
wherein the next correct nucleotide is a cognate nucleotide for the first allele or the 3' end of the primer comprises a cognate nucleotide for the first allele, and
wherein each of the stabilized ternary complexes is attached to the solid support via a linkage between the polymerase and the solid support or via a linkage between the next correct nucleotide and the solid support; and
(b) separating the solid support from the mixture of nucleic acids, thereby separating the first alleles from the second alleles at the plurality of loci.

* * * * *